United States Patent
Herrmann et al.

(10) Patent No.: US 7,855,310 B2
(45) Date of Patent: Dec. 21, 2010

(54) AH RECEPTOR ANTAGONISTS

(75) Inventors: Martina Herrmann, Hameln (DE); Oskar Koch, Göttingen (DE); Gabriele Vielhaber, Holzminden (DE); Jean Krutmann, Wegberg (DE)

(73) Assignee: SYMRISE GmbH & Co. KG, Holzminden (DE)

( * ) Notice: Subject to any disclaimer, the term of this patent is extended or adjusted under 35 U.S.C. 154(b) by 0 days.

(21) Appl. No.: 12/299,234

(22) PCT Filed: Apr. 30, 2007

(86) PCT No.: PCT/EP2007/054203

§ 371 (c)(1),
(2), (4) Date: Mar. 27, 2009

(87) PCT Pub. No.: WO2007/128723

PCT Pub. Date: Nov. 15, 2007

(65) Prior Publication Data

US 2009/0208433 A1 Aug. 20, 2009

Related U.S. Application Data

(60) Provisional application No. 60/796,855, filed on May 3, 2006.

(51) Int. Cl.
*C07C 45/00* (2006.01)
*A61K 31/122* (2006.01)

(52) U.S. Cl. ............ 568/313; 568/330; 514/680; 514/684

(58) Field of Classification Search ............ 568/313, 568/330; 514/680, 684
See application file for complete search history.

(56) References Cited

U.S. PATENT DOCUMENTS

2004/0147788 A1 7/2004 Savouret et al.

FOREIGN PATENT DOCUMENTS

| EP | 1317918 | 6/2003 |
|----|---------|--------|
| EP | 1484051 | 12/2004 |
| JP | 04134043 | 5/1992 |
| WO | WO-9925335 | 5/1999 |
| WO | WO-9956737 | 11/1999 |
| WO | WO-0249597 | 6/2002 |
| WO | WO-02056858 | 7/2002 |

OTHER PUBLICATIONS

Schreurs Richard H M M et al: "Examination of the in vitro (anti)estrogenic, (anti)androgenic and (anti)dioxin-like activities of tetraiin, indane and isochroman derivatives using receptor-specific bioassays." Toxicology Letters Apr. 10, 2005, vol. 156, No. 2, Apr. 10, 2005, pp. 261-275, XP002447004 ISSN: 0378-4274 abstract, Compound N13 in Table 2 is inactive at ArH receptor.
Database CA [Online], Chemical Abstracts Service, Columbus, Ohio, US; Kerbal, Abdelali et al.: "Cycloaddition of some diarylnitrilimines to various 2-arylidene-l-indanones. Regio- and diastereochemistry of spiropyrazoline synthesis" XPOO2447009 retrieved from STN Database accession No. 1989:94258 abstract compounds with CAS-RNs 17434-31-0 and 17434-32-1 (R1=R2=Me in formula I of application) & Bulletin des Societes Chimiques Belles 97(2), 149-61 Coden:BSCBAG; ISSN: 0037-9646, 1988.
Database CA [Online], Chemical Abstracts Service, Columbus, Ohio, US; Imbach, Jean L. et al: "Nuclear magnetic resonance spectra of derivatives of various substituted indanones and tetralones" XP002447010 retrieved from STN Database accession No. 1967:490264 abstract, compound with CAS-RN 17434-31-0 (R1=R2=Me in formula I of application) & Tetrahedron , 23(10), 3931-41 Coden: TETRAB; ISSN: 0040-4020, 1967.
Database Medline [Online], US National Library of Medicine (NLM), Bethesda, MD, US; Nov. 2005, Tauchi Masafumi et al: "Constitutive expression of aryl hydrocarbon receptor in keratinocytes causes inflammatory skin lesions." XP002447011 Database accession No. NLM16227587 abstract & Molecular and Cellular Biology Nov. 2005, vol. 25, No. 21, Nov. 2005, pp. 9360-9368, ISSN: 0270-7306 cited in the application.
Database Medline [Online], US National Library of Medicine (NLM), Bethesda, MD, US; Jan. 18, 2000, Shimizu Y et al: "Benzo[a]pyrene carcinogenicity is lost in mice lacking the aryl hydrocarbon receptor." XP002447012 Database accession No. NLM10639156 Abstract & Proceedings of the National Academy of Sciences of the United States of America Jan. 18, 2000, vol. 97, No. 2, Jan. 2000, pp. 779-782, ISSN: 0027-8424 cited in the application.

*Primary Examiner*—Sikarl A Witherspoon
(74) *Attorney, Agent, or Firm*—Connolly Bove Lodge & Hutz LLP

(57) ABSTRACT

The invention relates to the field of aryl hydrocarbon receptor (Ah receptor; AhR) antagonists and their uses.

21 Claims, 1 Drawing Sheet

AH RECEPTOR ANTAGONISTS

CROSS-REFERENCE TO RELATED APPLICATIONS

This application claims benefit of priority to PCT/EP054203 filed on Apr. 30, 2007, and published as WO 2007/128723 on Nov. 15, 2007, which asserts priority to U.S. Provisional Application No. 60/796,855, filed on May 3, 2006, which are incorporated herein by reference in their entireties.

The invention relates to the field of aryl hydrocarbon receptor (Ah receptor; AhR) antagonists and their uses.

The skin is the largest organ of the human body. Its most important function is to protect the body on the one hand against the uncontrolled escape of water, and on the other hand against the penetration of harmful chemicals or bacteria, as well as solar radiation.

The exposure of human skin to prolonged solar irradiation can give rise to many kinds of damage. Examples which may be mentioned here are sunburn, photoinduced skin ageing and skin cancer. This harmful action of sunlight is attributed inter alia to the UVB radiation (280-320 nm) contained in the spectrum of sunlight. It is necessary to protect the skin from UVB radiation as comprehensively as possible, particularly in view of the recent large increase in the intensity of the UVB component of the spectrum of sunlight due to the continuing destruction of the ozone layer.

To form a protective layer on the skin in order to protect against UV radiation, conventional sunscreens contain substances which absorb and/or reflect radiation in the 280-400 nm range (UV filters). Examples of such photoprotective substances are inorganic oxides like zinc oxide, or organic UV absorbers like cinnamic acid derivatives or dibenzoylmethane derivatives. However, a disadvantage of these compounds is that the protective layer they form can easily be destroyed by mechanical abrasion, water or detergents. It is therefore desirable to be able to have access not only to said UV filters, but also to substances that develop a protective action inside the skin.

In order to achieve this object, it is of fundamental importance to know the molecular mechanisms by which UVB radiation can cause unhealthy actions on human skin. Appropriate studies have shown that the biological actions of UVB radiation can be attributed in part to the fact that UVB radiation causes structural changes to the DNA molecules in the nucleus of skin cells. Accordingly, DNA repair enzymes are used to provide light protection (Stege et al. (2000) PNAS 97, 1790).

It has also been possible to demonstrate that UVB radiation is capable of triggering changes to the cell membrane that contribute to an activation of growth receptors, such as the epidermal growth factor receptor (EGF-R), and subsequently to tumour formation (Ashida et al. (2003) Exp. Dermatol. 12, 445; Lirvall et al. (1996) Biosci. Rep. 16, 227). This EGF-R activation can be inhibited by antioxidative enzymes (Lirvall et al. (1996) Biosci. Rep. 16, 227).

UVB and UVA light also induces the expression of cyclooxygenase-2 and matrix metalloproteinases (Pentland et al. (1999) Carcinogenesis 20(10), 1939-44). Cyclooxygenases belong to the key enzymes of the inflammatory reaction. They catalyse the first step of the synthesis of a number of inflammation mediators (prostaglandins, prostacyclins, thromboxanes) from arachidonic acid. There are 2 forms: cyclooxygenase-1 (COX-1) is the constitutive, continuously expressed form, whereas COX-2 is only expressed after stimulation by cellular signals, e.g. as a result of tissue damage or inflammation.

Matrix metalloproteinases (MMPs) are enzymes which are capable of proteolytically degrading the macromolecules of the extracellular matrix (ECM). MMPs possess a broad and often overlapping substrate specificity and, in combination, are capable of breaking down all the protein components of the extracellular matrix. About 20 MMPs have so far been identified. MMP-1 (collagenase-1), MMP-2 (gelatinase A), MMP-9 (gelatinase B) and MMP-3, in particular, play an important role in human skin. Apart from collagen-1 and -3, MMP-1 also cleaves Pro-MMP-2 and Pro-MMP-9, thereby activating them. MMP-2 and MMP-9 belong to the elastin-degrading proteases (A. Thibodeau, Cosmetics & Toiletries 2000, 115(11), 75-82).

It has been found that the content of MMPs is markedly greater in old skin than in young skin (J. H. Chung et al., J. Invest. Dermatol. 2001, 117, 1218-1224). MMPs also play a decisive role in the premature skin ageing due to exogenous factors. Thus it has also been possible to detect a higher level of MMPs in skin aged by light than in skin aged with protection from the light (J. H. Chung et al., J. Invest. Dermatol. 2001, 117, 1218-1224). The induction of matrix metalloproteinases has been demonstrated both for UVA and UVB radiation and for infrared radiation. It has been possible to observe this induction both in vitro on cultivated human dermal fibroblasts and in vivo on UV-irradiated human skin. Stimulation with tobacco smoke has also led to an up-regulation of the MMP expression in human dermal fibroblasts.

The aryl hydrocarbon receptor (AhR) (NCBI gene accession number BC0700800) has a central role in the detoxification of exogenous contaminants. It mediates the biological response to polycyclic aromatic hydrocarbons (PAHs) such as benz[a]pyrene and halogenated PAHs such as 2,3,7,8-tetrachlorodibenzo-p-dioxin (TCDD). The AhR is a ligand-activated transcription factor which, after binding a ligand, translocates into the cell nucleus, where it forms a dimer with another transcription factor, namely the aryl hydrocarbon receptor nuclear translocator (ARNT), binds to regulatory gene sequences and induces the transcription of various genes, e.g. CYP1A1 and CYP1B1. The consequences of AhR activation are the development of skin tumours (Shimizu et al. (2000) 97, 779), irritations and inflammations, the development of allergies, atopic dermatitis and itching, and a perturbation of skin integrity (Tauchi et al. (2005) Mol. Cell. Biol. 25, 9360-8; Henley at al., Arch. Biochem. Biophys. (2004) 422, 42-51), as well as the induction of MMP-1 (collagenase-1) (Murphy et al. (2004) J. Biol. Chem. 279, 25284-2593).

UVB light induces CYP1A1 expression in human keratinocytes and lymphocytes and in the mouse hepatoma cell line Hepa-1 (Wei et al., Chem. Biol. Interact. (1999) 118, 127-40). However, it has only been demonstrated for Hepa-1 cells that CYP1A1 induction is AhR-dependent, but, as explained below, AhR activation is dependent on the cell type, so it is not possible to extrapolate from the action on mouse hepatoma cells to the action on human skin cells. Moreover, CYP1A1 can also be induced by AhR-independent pathways (Guigal et al. (2001) Life Sci. 68(18), 2141-50; Tijet et al. (2006) Mol. Pharmacol. 69(1), 140-153). Therefore, there is not necessarily a connection between UVB, the AhR and CYP1A1 in keratinocytes.

WO 99/56737 discloses stilbenes as ligands of the Ah receptor. Although some stilbenes are said to bind to the Ah receptor, none of them effects CYP1A1 induction. These stilbenes include 3,4,3',5-tetrahydroxystilbene, or piceatannol, 2,3',4,5'-tetrahydroxystilbene, or oxyresveratrol, and 3,5,4'-trihydroxystilbene, or resveratrol, especially trans-resveratrol. A photoprotective action, particularly against UVB radiation, is not described. A disadvantage of stilbenes is that they are photolabile and frequently elicit endocrine actions. For example, resveratrol is an antiandrogen (Mitchell et al. (1999) Cancer Res. 59, 5892-5895).

Henry et al. ((1999) Mol. Pharmacol. 55, 716-25) describe 3-methoxylated flavones, carrying an electron-withdrawing substituent in the 4-position, as effective AhR antagonists in liver cells. Joiakim et al. ((2003) Drug Metab. Dispos. 31, 1279-82) showed that the Jun N-terminal kinase inhibitor anthra[1,9-cd]pyrazol-6(2H)-one can inhibit the action of the potent AhR agonist 2,3,7,8-tetrachlorodibenzo-p-dioxin (TCDD) in human breast epithelial cells.

Binding to the AhR is furthermore dependent on the cell type. Zhang et al. ((2003) Environ. Health Perspec. 111, 1877-1882) have found that e.g. quercetin prevents the action of the AhR in the human breast cancer cell line MCF-7, but has no effect on the human liver cancer cell line HepG2. An opposite effect was found for luteolin, which has no effect on MCF-7 cells but acts as an AhR inhibitor in HepG2 cells. Differences were also found in the ligand affinity of the AhR between human cells and rodent cells (Ema et al. (1994) J. Biol. Chem. 269, 27337-43; Zhang et al. (2003) Environ. Health Perspec. 111, 1877-1882).

Scarcely any compounds are known which function as AhR antagonists in human skin cells. Although curcumin inhibits AhR activation by the tobacco carcinogen benz[a]pyrene-7R-trans-7,8-dihydrodiol in oral human keratinocyte cancer cells and in ex vivo oral mucosa, it activates AhR translocation in the absence of the tobacco carcinogen (Rinaldi et al. (2002) Cancer Res. 62, 5451-5456) and hence is not an AhR antagonist in terms of the invention.

It is further known that all-trans-retinoic acid inhibits TCDD-induced AhR activation in normal human keratinocytes without influencing AhR activity in the absence of TCDD. All-trans-retinoic acid also has the considerable disadvantage of boosting the TCDD-induced expression of MMP-1 (Murphy et al. (2004) J. Biol. Chem. 279, 25284-25293) and is photolabile.

The object of the invention was therefore to provide substances which act as Ah receptor antagonists without exhibiting the disadvantages of the state of the art as described above.

In terms of this invention, a gene is referred to as induced if the concentration of the corresponding mRNA in the presence of the allocated inductor is significantly higher (p<0.05, Student's t-test), i.e. at least 10% higher, than in the absence of the inductor.

According to the invention, it has now been found that compounds of general formula (I):

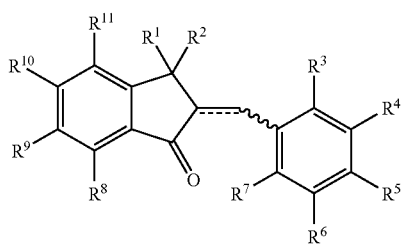

(I)

in which
$R^1$ and $R^2$ independently of one another are hydrogen or $C_1$-$C_{12}$-alkyl,
$R^3$ to $R^{11}$ independently of one another are hydrogen, $C_1$-$C_{12}$-alkyl, hydroxyl or $C_1$-$C_{12}$-alkoxy, and
the broken line represents either a double bond or two hydrogens,
are effective as AhR antagonists.

In particular, according to the invention, substances of general formula (I) in which neither $R^1$ nor $R^2$ is H are provided for the first time.

Substances of the formula below:

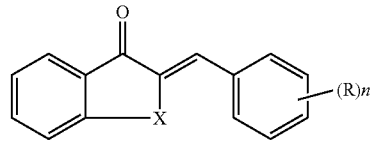

in which
X=$C_{1-3}$-alkylene, CO, O, S, $C_{1-2}$-oxyalkylene or $C_{1-2}$-thioalkylene,
R=OH, alkoxy, alkenyloxy, aralkoxy, carboxyl, alkoxycarbonyl or aminocarbonyl, and
n=1-3, are known from JP-O4,134,043 (1992) as UV absorbers, but not as AhR antagonists.

Surprisingly, the compounds of formula (I) have proved to be very effective Ah receptor antagonists. In human skin cells they can prevent the UVB-induced translocation of the AhR from the cytoplasm into the cell nucleus. They greatly reduce the AhR-mediated induction of AhR-inducible genes in human skin cells (particularly in keratinocytes), and especially the induction of CYP1A1. They are photostable and, in the absence of an AhR-activating substance, especially AhR inductors such as polycyclic aromatic hydrocarbons and their halogenated derivatives, particularly TCDD, or AhR inductors formed in skin cells (like keratinocytes), such as 6-formylindolo[3,2-b]carbazole (FICZ), do not trigger the induction of an AhR-inducible gene, nor do they induce the translocation of the AhR from the cytoplasm into the nucleus of human skin cells, in contrast to e.g. curcumin and all-trans-retinoic acid.

Surprisingly, the compounds of formula (I), especially those of formulae (Ia) and (Ib), also have a skin-lightening action.

The compounds of formula (I) are therefore particularly suitable as drugs, especially for treating or preventing (particularly UVB-induced) skin irritations, skin damage, skin inflammations, itching, atopic dermatitis, skin ageing and skin cancer, and/or for reducing the MMP content of the skin. Furthermore, as drugs or in a non-drug form (especially in cosmetic form), the compounds are suitable for reducing or preventing a translocation of the AhR into a cell nucleus, reducing or preventing a UVB-induced gene expression, and/or reducing or preventing a gene expression induced by AhR agonists. In this respect the compounds of formula (I) are suitable for protecting skin cells (especially keratinocytes) from environmental toxins, and for detoxification, especially with reference to AhR inductors such as polycyclic aromatic hydrocarbons and their halogenated derivatives, particularly TCDD, or AhR inductors formed in skin cells, such as 6-formylindolo[3,2-b]carbazole (FICZ). The compounds of formula (I) are also suitable as sunscreens and especially as UVB filters.

Compounds of formula (I) according to the invention can be prepared e.g. by reacting appropriate indanones with aromatic aldehydes (aldol condensation). This reaction is preferably carried out in the presence of a base and particularly preferably in the presence of a strong inorganic base such as LiOH, NaOH or KOH. The indanones can be obtained e.g. analogously to the synthetic pathways described in DE 100 55 940 (corresponding to WO 02/38537) or WO 03/076379. The following reaction scheme illustrates the preferred synthetic pathway for the preparation of the compounds of formula (I) according to the invention:

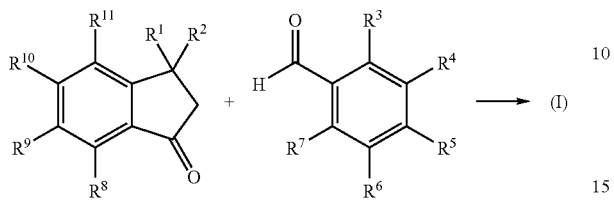

in which the radicals $R^1$ to $R^{11}$ are as defined above (or have the particular preferred meanings mentioned below).

Preferred compounds according to the invention are those in which $R^1$ and $R^2$ independently of one another are methyl. Preferably, $R^1$ and $R^2$ are both methyl simultaneously. Other preferred compounds are those in which no more than four of the radicals $R^3$ to $R^{11}$ are not hydrogen, at least one and at most four of the radicals $R^3$ to $R^{11}$ independently of one another preferably being hydroxyl, $C_1$-$C_4$-alkyl (branched or unbranched) or $C_1$-$C_4$-alkoxy. In preferred embodiments, if one of the radicals is hydroxyl or $C_1$-$C_4$-alkoxy, the remaining radicals, i.e. at most three, can be H or $C_1$-$C_4$-alkyl (branched or unbranched), it further being preferable for both $R^1$ and $R^2$ to be methyl simultaneously. Compounds substituted in this way have proved to be particularly effective AhR antagonists.

Particularly preferred compounds are those of formulae (Ia), (Ib), (Ic) and (Id), which can exist as (E) and/or (Z) isomers:

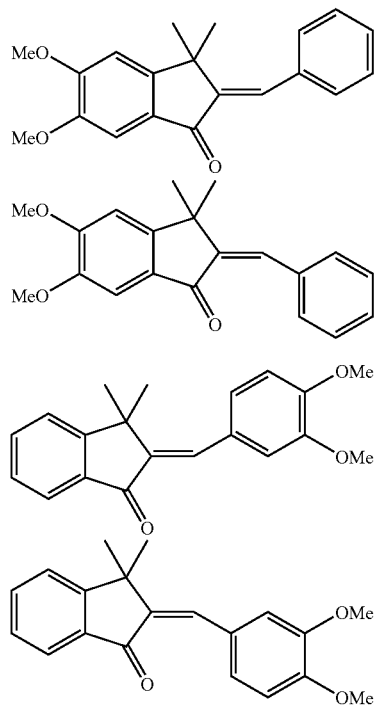

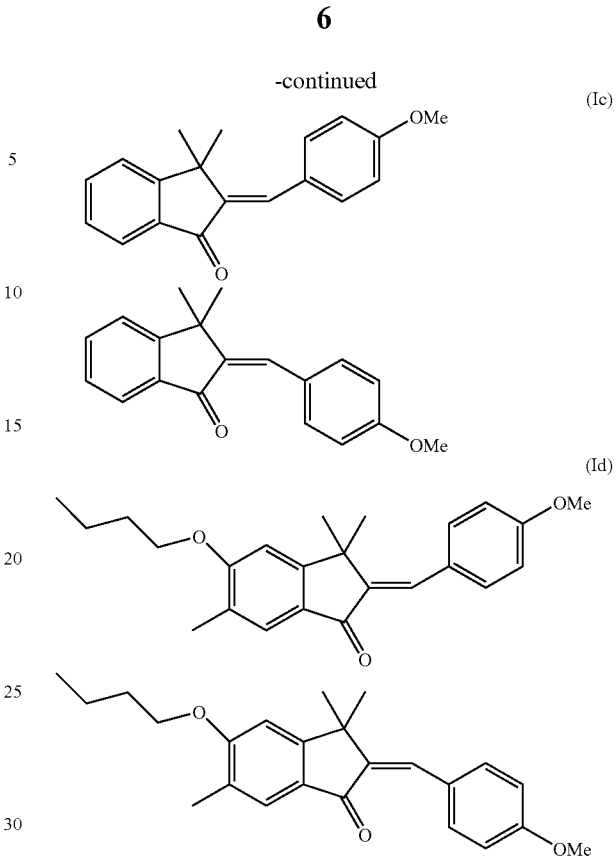

the compounds of formulae (Ia) and (Ib) being particularly preferred and the compounds of formula (Ia) being very particularly preferred. These compounds are particularly photostable, afford a strong inhibition of the Ah receptor, even in very low use concentrations, and prevent or reduce the AhR-mediated induction of AhR-inducible genes, especially CYP1A1, even in low concentrations. Furthermore, the compounds of formulae (I), preferably those of formulae (Ia), (Ib), (Ic) and (Id) and especially the compounds of formulae (Ia) and (Ib), in the absence of UVB radiation and/or an AhR inductor, especially AhR inductors such as polycyclic aromatic hydrocarbons and their halogenated derivatives, particularly TCDD, or AhR inductors formed in skin cells (like keratinocytes), such as 6-formylindolo[3,2-b]carbazole (FICZ), do not themselves induce an AhR-inducible gene, especially CYP1A1, nor do they induce the translocation of the AhR from the cytoplasm into the cell nucleus under these conditions. The compounds of formulae (Ia) and (Ib) are therefore particularly suitable for the above-described uses of AhR antagonists and are especially preferred as drugs.

Furthermore, according to the invention, formulations are provided which contain one or more compounds of formula (I), preferably of formulae (Ia), (Ib), (Ic) and/or (Id) and especially of formulae (Ia) and/or (Ib). Expediently, the compounds of formula (I), preferably of formulae (Ia), (Ib), (Ic) and/or (Id) and especially of formulae (Ia) and/or (Ib), are present in formulations according to the invention in a sufficient amount (a) to reduce or prevent a translocation of the AhR into a cell nucleus, (b) to reduce or prevent a UVB-induced gene expression, and/or (c) to reduce or prevent a TCDD-induced gene expression.

The formulations according to the invention contain the compound(s) of formula (I), preferably the compound(s) of formulae (Ia), (Ib), (Ic) and/or (Id) and especially of formulae (Ia) and/or (Ib), in a concentration preferably of at least 0.00001 wt. %, based on the total composition. In these concentrations, especially in the case of the compound of formula (Ia), it is already possible to observe a reduction in the translocation of the AhR receptor into the nucleus of skin cells, and also the induction of AhR-inducible genes, especially CYP1A1, by AhR agonists such as TCDD is already significantly reduced.

Preferably, the concentration of the compound(s) of formula (I), preferably the compound(s) of formulae (Ia), (Ib), (Ic) and/or (Id) and especially of formulae (Ia) and/or (Ib), is 0.0001 to 10 wt. %, particularly preferably 0.001 to 5 wt. % and especially 0.01 to 1 wt. %, based in each case on the total composition. When applied to the skin in these concentrations, the compounds of formulae (I) develop a strong AhR-antagonistic action in that they prevent or reduce the translocation of the AhR into the cell nucleus and, in particular, reduce or prevent a UVB-induced gene expression, specifically of CYP1A1.

The formulations can be especially cosmetic formulations, particular preference being afforded to sunscreen formulations, skin protection lotions and after-sun formulations (e.g. sun creams and after-sun lotions).

The cosmetic or therapeutic formulations according to the invention are prepared by conventional processes known per se, wherein the compound(s) of formula (I), preferably the compound(s) of formulae (Ia), (Ib), (Ic) and/or (Id) and especially of formulae (Ia) and/or (Ib), is (are) incorporated into cosmetic or dermatological formulations which are of conventional composition and, in addition to their skin-lightening and hair-lightening action, can also be used to treat, care for and clean the skin or hair.

The formulations according to the invention preferably take the form of an emulsion, e.g. an emulsion of the W/O (water-in-oil) type, O/W (oil-in-water) type, W/O/W (water-in-oil-in-water) type or O/W/O (oil-in-water-in-oil) type, a PIT emulsion, a Pickering emulsion, an emulsion with a low oil content, or a microemulsion or nanoemulsion, a solution, e.g. in oil (fatty oils or fatty acid esters, especially $C_6$-$C_{32}$ fatty acid $C_2$-$C_{30}$ esters) or silicone oil, a dispersion, a suspension, a cream, a lotion or milk, depending on the preparative process and the ingredients, a gel (including hydrogel, hydrodispersion gel, oleogel), a spray (e.g. pump spray or spray with propellant) or else a foam or an impregnating solution for cosmetic tissues, a cleaning product, e.g. soap, syndet, liquid wash, shower or bath preparation, a bath product (capsule, oil, tablet, salt, bath salt, soap, etc.), an effervescent formulation, a skin care product such as an emulsion (as described above), an ointment, a paste, a gel (as described above), an oil, a toner, a balsam, a serum or a powder (e.g. face powder, body powder), a mask, a pencil, a stick, a roll-on, a pump, an aerosol (foaming, non-foaming or after-foaming), a deodorant and/or antiperspirant, a gargle or mouthwash, a foot care product (including keratolytic, deodorant), an insect repellent, a sunscreen, a self-tanning product and/or after-sun preparation, a skin toner, a shaving product, an after-shave balm, a pre-shave or after-shave lotion, a depilatory, a hair care product, e.g. a shampoo (including 2-in-1 shampoo, antidandruff shampoo, baby shampoo, shampoo for dry scalp, shampoo concentrate), a conditioner, a hair treatment, a hair tonic, a hair rinse, a styling cream, a pommade, a perming product or fixer, a hair setting lotion (spray), a styling aid (e.g. gel or wax), a hair smoothing product (straightener, relaxer), a bleach, a hair colourant, e.g. temporary, direct hair colourant, semipermanent hair colourant or permanent hair colourant, a hair toner, a hair lightener, a hair conditioner, a hair mousse, an eye care product, a make-up, a make-up remover or a baby product.

It is also advantageous to administer the compound(s) of formula (I), preferably the compound(s) of formulae (Ia), (Ib), (Ic) and/or (Id), especially of formulae (Ia) and/or (Ib), in encapsulated form, e.g. in gelatin, wax materials, liposomes or cellulose capsules.

Particularly preferably, the formulations according to the invention take the form of an emulsion, especially an emulsion of the W/O, O/W, W/O/W or O/W/O type, a PIT emulsion, a Pickering emulsion, an emulsion with a low oil content, or a microemulsion or nanoemulsion, a gel (including hydrogel, hydrodispersion gel, oleogel), a solution, e.g. in oil (fatty oils or fatty acid esters, especially $C_6$-$C_{32}$ fatty acid $C_2$-$C_{30}$ esters) or silicone oil, or a spray (e.g. pump spray or spray with propellant).

The (particularly topical) cosmetic or therapeutic formulations according to the invention can preferably contain cosmetic and/or dermatological auxiliary substances and additives such as those conventionally used in such formulations, e.g. cooling agents, warming agents, sunscreens (especially UV filters and/or UV-filtering pigments), dyes, pigments with a colouring action, antioxidants, preservatives, anti-irritants, softeners, moisturizers and/or moisture retainers (moisture retention regulators, e.g. glycerol or urea), osmolytes, antimicrobials (e.g. antibacterials, bactericides, fungicides), virucides, deodorants (e.g. antiperspirants), surface-active substances (surfactants), emulsifiers, insect repellents (e.g. DEET, IR 3225, Dragorepel), plant extracts, anti-inflammatories, cicatrizants (e.g. chitin or chitosan and chitosan derivatives), gelling agents, film-forming substances (e.g. polyvinylpyrrolidones or chitosan or chitosan derivatives), fixatives, skin smoothing substances, antiwrinkle substances such as beta-glucan from oats, blackberry extract or soya extract, vitamins (e.g. vitamin C and derivatives, tocopherols and derivatives, vitamin A and derivatives), 2-hydroxycarboxylic acids (e.g. citric acid, malic acid, L-, D- or DL-lactic acid), skin colourants (e.g. walnut extracts or dihydroxyacetone), skin care and repair agents (e.g. cholesterol, ceramides, pseudoceramides, creatine and creatine esters), skin soothing agents, superfatting agents, optical brighteners, lubricants, lustre agents, fats, oils, saturated fatty acids and salts thereof, monounsaturated or polyunsaturated fatty acids and salts thereof, alpha-hydroxy acids, polyhydroxy fatty acids or derivatives thereof (e.g. linoleic acid, alpha-linolenic acid, gamma-linolenic acid or arachidonic acid and natural or synthetic esters thereof), phospholipids, waxes or other conventional constituents of a cosmetic or dermatological formulation, such as alcohols, alkanediols, polyols, polymers, electrolytes, organic solvents, silicones, silicone derivatives or chelating agents (e.g. ethylenediaminetetraacetic acid and derivatives), antidandruff agents (e.g. climbazole, ketoconazole, piroctonoleamine, zinc pyrithione), hair care agents, hair deforming agents, hair smoothing agents, depilatories, perfumes, ethereal oils, foaming agents, foam stabilizers, foam boosters, antifoams, thickeners, binders, plant parts (e.g. fibres) and plant extracts (e.g. arnica, aloe, beard lichen, ivy, stinging nettle, ginseng, henna, chamomile, marigold, rosemary, sage, horsetail or thyme), animal extracts, e.g. royal jelly, propolis, proteins or protein hydrolysates, yeast extracts, hop and wheat extracts, peptides or thymus extracts, abrasives, buffers and enzymes.

Constituents (auxiliary substances and additives) with which the compound(s) of formula (I), preferably the compound(s) of formulae (Ia), (Ib), (Ic) and/or (Id) and especially of formulae (Ia) and/or (Ib), can be combined are particularly preferred:

abrasives, antidandruff agents, anti-inflammatories, antioxidants, antiperspirants, binders, buffers, chelating agents, depilatories, surface-active substances, emulsifiers, enzymes, ethereal oils, plant extracts, fibres, film-forming agents, fixatives, foaming agents, foam stabilizers, antifoams, foam boosters, gelling agents, hair care agents, hair deforming agents, hair smoothing agents, skin and hair lighteners, moisturizers, moisture retainers, insect repellents, optical brighteners, lubricants, lustre agents, polymers, proteins, superfatting agents, skin soothing agents, skin smoothing agents, antiwrinkle agents, sunscreens, vitamins, oils, waxes, fats, phospholipids, saturated fatty acids and salts thereof, monounsaturated or polyunsaturated fatty acids and salts thereof, alpha-hydroxy acids, polyhydroxy fatty acids, polyols, alkanediols, silicones or silicone derivatives.

Auxiliary substances and additives can be present in amounts of 5 to 99 wt. %, preferably of 10 to 80 wt. %, based on the total weight of the formulation. The amounts of cosmetic or dermatological auxiliary substances and additives and perfume to be used in each case can easily be determined by those skilled in the art, according to the particular type of product, using simple trial and error.

The formulations can also contain water in an amount of up to 99.99 wt. %, preferably of 5 to 80 wt. %, based on the total weight of the formulation.

Cosmetic or therapeutic formulations according to the invention are preferably formulations which are selected from the group comprising:

an emulsion, a solution, a dispersion, a suspension, a cream, a lotion, a milk, a gel, a spray, a foam, an impregnating solution for cosmetic tissues, a cleaning product, a soap, a syndet, a wash preparation, a shower preparation, a bath preparation, a bath product, an effervescent formulation, a skin care product, an ointment, a paste, an oil, a toner, a balsam, a serum, a powder, a mask, a pencil, a stick, a roll-on, a pump, an aerosol, a deodorant, an antiperspirant, a gargle, a mouthwash, a foot care product, an insect repellent, a sunscreen, a self-tanning product, an after-sun preparation, a skin toner, a shaving product, an after-shave balm, a pre-shave lotion, an after-shave lotion, a depilatory, a hair care product, a shampoo, a conditioner, a hair treatment, a hair tonic, a hair rinse, a styling cream, a pommade, a perming product, a fixer, a hair setting lotion, a styling aid, a hair smoothing product, a bleach, a hair colourant, a hair toner, a hair lightener, a hair conditioner, a hair mousse, an eye care product, a make-up, a make-up remover and a baby product, and/or which, in addition to the compound(s) of formula (I), preferably compound(s) of formulae (Ia), (Ib), (Ic) and/or (Id) and especially of formulae (Ia) and/or (Ib), contain one or more auxiliary substances and additives selected from the group comprising:

abrasives, antidandruff agents, anti-inflammatories, antioxidants, antiperspirants, binders, buffers, chelating agents, depilatories, surface-active substances, emulsifiers, enzymes, ethereal oils, plant extracts, fibres, film-forming agents, fixatives, foaming agents, foam stabilizers, antifoams, foam boosters, gelling agents, hair care agents, hair deforming agents, hair smoothing agents, skin and hair lighteners, moisturizers, moisture retainers, insect repellents, optical brighteners, lubricants, lustre agents, polymers, proteins, superfatting agents, skin soothing agents, skin smoothing agents, antiwrinkle agents, sunscreens, vitamins, oils, waxes, fats, phospholipids, saturated fatty acids and salts thereof, monounsaturated or polyunsaturated fatty acids and salts thereof, alpha-hydroxy acids, polyhydroxy fatty acids, polyols, alkanediols, silicones and silicone derivatives, and/or which are intended for application to the hair and/or skin.

For use, the formulations containing the compound(s) of formula (I), preferably compound(s) of formulae (Ia), (Ib), (Ic) and/or (Id) and especially of formulae (Ia) and/or (Ib), are normally applied to the skin and/or hair in a sufficient amount and in a manner customary for cosmetic and skin preparations. Cosmetic, dermatological and/or therapeutic formulations according to the invention which additionally comprise one or more sunscreens (UV absorbers, UV filters) are particularly advantageous.

In rare cases, formulations containing compounds of formula (I) according to the invention, or to be used according to the invention, can experience discolouration and/or instability, especially if they are in aqueous-alcoholic or purely alcoholic solution. Surprisingly, it has now been found that UV filters can improve the stability of the compounds of formula (I) in formulations according to the invention. In particular, UV filters can prevent or retard a discolouration of the compounds of formula (I) due to sunlight or other light. Both are important, especially in cosmetic formulations. According to the invention, UV filters are therefore used to stabilize the compounds of formula (I), especially by using one or more UV filters in a sufficient amount to stabilize the compounds of formula (I) in a formulation according to the invention, and preferably using the UV filters mentioned below (as preferred). In this context a further feature of the invention relates to the cosmetic or therapeutic use of one or more compounds of formula (I) for lightening skin and/or hair in the presence of one or more UV filters in an amount that stabilizes the compound(s) of formula (I), preferably the compound(s) of formulae (Ia), (Ib), (Ic) and/or (Id) and especially of formulae (Ia) and/or (Ib), all the details given above on the choice of substituents naturally applying in this case as well. For the purposes of stabilization, the total amount of UV filters preferably ranges from 0.1 to 2 wt. %, especially from 0.2 to 1 wt. %, based on the total weight of the formulation.

The ratio of the total proportion by weight of UV filters to the total proportion by weight of compounds of formula (I) according to the invention, or to be used according to the invention, ranges preferably from 100:1 to 1:100, particularly preferably from 10:1 to 1:10 and very particularly preferably from 5:1 to 1:5.

Formulations according to the invention which contain one or more UV filters (sunscreens, UV absorbers) have a total proportion of UV filters ranging preferably from 0.1 to 30 wt. %, particularly preferably from 0.2 to 20 wt. % and very particularly preferably from 0.5 to 15 wt. %, based on the total weight of the formulation. Particularly preferably, the formulations according to the invention contain one or more UVB filters, especially of the types indicated below. It has been found that the substances of formula (I) according to the invention, preferably of formulae (Ia), (Ib), (Ic) and/or (Id) and especially of formulae (Ia) and/or (Ib), interact advantageously with UVB filters to prevent UVB-induced skin damage, skin changes and skin cancer.

Particularly preferably, the compounds of formula (I) according to the invention, or to be used according to the invention, and especially those of formulae (Ia), (Ib), (Ic) and (Id), are combined with water-soluble UV filters; in one preferred embodiment, they are combined with disodium phenylenebisbenzimidazyltetrasulfonate (Neo Heliopan® AP) and/or 2-phenylbenzimidazolesulfonic acid (Neo Heliopan® Hydro) and salts thereof.

In another preferred embodiment, a formulation according to the invention contains sunscreens, i.e. especially UV filters and/or inorganic pigments (UV-filtering pigments), in a total amount such that the formulation according to the invention has a light protection factor greater than or equal to 2 (preferably greater than or equal to 5). Such formulations according to the invention are particularly suitable for protecting the skin and hair.

Formulations according to the invention which additionally comprise one or more sunscreens (UV filters, UV absorbers) can take a variety of forms such as those conventionally used e.g. for sunscreen formulations. For example, they can be in the form of an emulsion of the oil-in-water (O/W) type, a gel, a hydrodispersion or an aerosol.

Advantageously, the formulations according to the invention contain at least one UVA filter and/or at least one UVB filter and/or a broadband filter and/or at least one inorganic pigment. Formulations according to the invention preferably contain at least one UVB filter or a broadband filter and particularly preferably contain at least one UVA filter and at least one UVB filter.

Examples of suitable UV filters are organic UV absorbers from the class comprising 4-aminobenzoic acid and derivatives, salicylic acid derivatives, benzophenone derivatives, dibenzoylmethane derivatives, diphenyl acrylates, 3-imidazol-4-ylacrylic acid and esters thereof, benzofuran derivatives, benzylidenemalonate derivatives, polymeric UV absorbers containing one or more silicon-organic radicals, cinnamic acid derivatives, camphor derivatives, trianilino-s-triazine derivatives, 2-hydroxyphenylbenzotriazole derivatives, phenylbenzimidazolesulfonic acid derivatives and salts thereof, menthyl anthranilate, benzotriazole derivatives and indole derivatives.

The UV filters mentioned below, which can be used for the purposes of the present invention, are preferred but of course do not imply a limitation.

Advantageous UV filters are:

UVB filters such as:
  p-aminobenzoic acid
  ethoxylated ethyl p-aminobenzoate (25 mol of EO) (INCI name: PEG-25 PABA)
  2-ethylhexyl p-dimethylaminobenzoate
  N-propoxylated ethyl p-aminobenzoate (2 mol of PO)
  glyceryl p-aminobenzoate
  homomethyl salicylate (homosalate) (Neo Heliopan® HMS)
  2-ethylhexyl salicylate (Neo Heliopan® OS)
  triethanolamine salicylate
  4-isopropylbenzyl salicylate
  menthyl anthranilate (Neo Heliopan® MA)
  ethyl diisopropylcinnamate
  2-ethylhexyl p-methoxycinnamate (Neo Heliopan® AV)
  methyl diisopropylcinnamate
  isoamyl p-methoxycinnamate (Neo Heliopan® E 1000)
  diethanolamine p-methoxycinnamate
  isopropyl p-methoxycinnamate
  2-phenylbenzimidazolesulfonic acid and salts (Neo Heliopan® Hydro)
  3-(4'-trimethylammonium)benzylidenebornan-2-one methylsulfate
  beta-imidazol-4(5)-acrylic acid (urocanic acid)
  3-(4'-sulfo)benzylidenebornan-2-one and salts
  3-(4'-methylbenzylidene)-D,L-camphor (Neo Heliopan® MBC)
  3-benzylidene-D,L-camphor
  N-[(2 and 4)-[2-(oxoborn-3-ylidene)methyl]benzyl]acrylamide polymer
  4,4'-[(6-[4-(1,1-dimethylaminocarbonyl)phenylamino]-1,3,5-triazine-2,4-diyl)diimino]bis(2-ethylhexyl benzoate) (Uvasorb® HEB)
  benzylidenemalonate-polysiloxane (Parsol® SLX)
  glyceryl ethylhexanoate dimethoxycinnamate
  dipropylene glycol salicylate
  tris(2-ethylhexyl) 4,4',4"-(1,3,5-triazine-2,4,6-triyltriimino)tribenzoate (=2,4,6-trianilino(p-carbo-2'-ethylhexyl-1'-oxy)-1,3,5-triazine) (Uvinul® T150)

broadband filters such as:
  2-ethylhexyl 2-cyano-3,3-diphenylacrylate (Neo Heliopan® 303)
  ethyl 2-cyano-3,3'-diphenylacrylate
  2-hydroxy-4-methoxybenzophenone (Neo Heliopan® BB)
  2-hydroxy-4-methoxybenzophenone-5-sulfonic acid
  dihydroxy-4-methoxybenzophenone
  2,4-dihydroxybenzophenone
  tetrahydroxybenzophenone
  2,2'-dihydroxy-4,4'-dimethoxybenzophenone
  2-hydroxy-4-n-octyloxybenzophenone
  2-hydroxy-4-methoxy-4'-methylbenzophenone
  sodium hydroxymethoxybenzophenonesulfonate
  disodium 2,2'-dihydroxy-4,4'-dimethoxy-5,5'-disulfobenzophenone
  2-(2H-benzotriazol-2-yl)-4-methyl-6-(2-methyl-3-(1,3,3,3-tetramethyl-1-(trimethylsilyl)oxy)disiloxanyl)propylphenol (Mexoryl® XL)
  2,2'-methylenebis(6-(2H-benztriazol-2-yl)-4-(1,1,3,3-tetramethylbutyl)phenol) (Tinosorb® M)
  2,4-bis[4-(2-ethylhexyloxy)-2-hydroxyphenyl]-1,3,5-triazine
  2,4-bis[{4-(2-ethylhexyloxy)-2-hydroxy}phenyl]-6-(4-methoxyphenyl)-1,3,5-triazine (Tinosorb® S)
  2,4-bis[{(4-(3-sulfonato)-2-hydroxypropoxy)-2-hydroxy}phenyl]-6-(4-methoxyphenyl)-1,3,5-triazine sodium salt
  2,4-bis[{(3-(2-propoxy)-2-hydroxypropoxy)-2-hydroxy}phenyl]-6-(4-methoxyphenyl)-1,3,5-triazine
  2,4-bis[{4-(2-ethylhexyloxy)-2-hydroxy}phenyl]-6-[4-(2-methoxyethylcarbonyl)phenylamino]-1,3,5-triazine
  2,4-bis[{4-(3-(2-propoxy)-2-hydroxypropoxy)-2-hydroxy}phenyl]-6-[4-(2-ethylcarboxyl)phenylamino]-1,3,5-triazine
  2,4-bis[{4-(2-ethylhexyloxy)-2-hydroxy}phenyl]-6-(1-methylpyrrol-2-yl)-1,3,5-triazine
  2,4-bis[{4-tris(trimethylsiloxysilylpropoxy)-2-hydroxy}phenyl]-6-(4-methoxyphenyl)-1,3,5-triazine
  2,4-bis[{4-(2"-methylpropenyloxy)-2-hydroxy}phenyl]-6-(4-methoxyphenyl)-1,3,5-triazine
  2,4-bis[{4-(1',1',1',3',5',5',5'-heptamethylsiloxy-2"-methylpropoxy)-2-hydroxy}phenyl]-6-(4-methoxyphenyl)-1,3,5-triazine UVA filters such as:
  4-isopropyldibenzoylmethane
  terephthalylidenedibornanesulfonic acid and salts (Mexoryl® SX)
  4-t-butyl-4'-methoxydibenzoylmethane (avobenzone) (Neo Heliopan® 357)
  Disodium phenylenebisbenzimidazyltetrasulfonate (Neo Heliopan® AP)

monosodium 2,2'-(1,4-phenylene)bis(1H-benzimidazole-4,6-disulfonate)

hexyl 2-(4-diethylamino-2-hydroxybenzoyl)benzoate (Uvinul® A Plus)

indanylidene compounds according to DE 100 55 940 (=WO 02/38537)

The following UV filters are particularly suitable for combination:

p-aminobenzoic acid 3-(4'-trimethylammonium)benzylidenebornan-2-one methylsulfate homomethyl salicylate (Neo Heliopan® HMS)

2-hydroxy-4-methoxybenzophenone (Neo Heliopan® BB)

2-phenylbenzimidazolesulfonic acid (Neo Heliopan® Hydro)

terephthalylidenedibornanesulfonic acid and salts (Mexoryl® SX)

4-tert-butyl-4'-methoxydibenzoylmethane (Neo Heliopan® 357)

3-(4'-sulfo)benzylidenebornan-2-one and salts 2-ethylhexyl 2-cyano-3,3-diphenylacrylate (Neo Heliopan® 303)

N-[(2 and 4)-[2-(oxoborn-3-ylidene)methyl]benzyl]acrylamide polymer 2-ethylhexyl p-methoxycinnamate (Neo Heliopan® AV)

ethoxylated ethyl p-aminobenzoate (25 mol of EO) (INCI name: PEG-25 PABA)

isoamyl p-methoxycinnamate (Neo Heliopan® E1000)

2,4,6-trianilino(p-carbo-2'-ethylhexyl-1'-oxy)-1,3,5-triazine (Uvinul® T150)

2-(2H-benzotriazol-2-yl)-4-methyl-6-(2-methyl-3-(1,3,3,3-tetramethyl-1-(trimethylsilyl)oxy)disiloxanyl)propylphenol (Mexoryl® XL)

4,4'-[(6-[4-(1,1-dimethyl)aminocarbonyl)phenylamino]-1,3,5-triazine-2,4-diyl)diimino]bis(2-ethylhexyl benzoate) (Uvasorb HEB)

3-(4'-methylbenzylidene)-D,L-camphor (Neo Heliopan® MBC)

3-benzylidenecamphor 2-ethylhexyl salicylate (Neo Heliopan® OS)

2-ethylhexyl 4-dimethylaminobenzoate (Padimate O)

hydroxy-4-methoxybenzophenone-5-sulfonic acid and Na salt 2,2'-methylenebis(6-(2H-benztriazol-2-yl)-4-(1,1,3,3-tetramethylbutyl)phenol) (Tinosorb® M)

disodium phenylenebisbenzimidazyltetrasulfonate (Neo Heliopan® AP)

2,4-bis[{4-(2-ethylhexyloxy)-2-hydroxy}phenyl]-6-(4-methoxyphenyl)-1,3,5-triazine (Tinosorb® S)

benzylidenemalonate-polysiloxane (Parsol® SLX)

menthyl anthranilate (Neo Heliopan® MA)

hexyl 2-(4-diethylamino-2-hydroxybenzoyl)benzoate (Uvinul® A Plus)

indanylidene compounds according to DE 100 55 940 (=WO 02/38537)

It is also possible to use particulate UV filters or inorganic pigments, which can optionally be hydrophobized, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$) and cerium (e.g. $Ce_2O_3$) and/or mixtures thereof.

Formulations according to the invention, especially dermatological formulations, can also advantageously contain dyes and/or coloured pigments, particularly if they are to be used in the field of decorative cosmetics. The dyes and coloured pigments can be selected from the appropriate list approved by the cosmetics regulations or from the EC list of cosmetic colourants. In most cases they are identical to the dyes permitted for use in foods. Examples of advantageous coloured pigments are titanium dioxide, mica, iron oxides (e.g. $Fe_2O_3$, $Fe_3O_4$, FeO(OH)) and/or tin oxide. Examples of advantageous dyes are carmine, Berlin blue, chrome oxide green, ultramarine blue and/or manganese violet.

Specific cooling agents preferably used within the framework of the present invention are listed below. Those skilled in the art can add a large number of other cooling agents to this list; the cooling agents listed can also be used in combination with one another: L-menthol, D-menthol, racemic menthol, menthone glycerol acetal (trade name: Frescolat® MGA), menthyl lactate (trade name: Frescolat® ML; menthyl lactate is preferably L-menthyl lactate, especially L-menthyl L-lactate), substituted menthyl-3-carboxamides (e.g. menthyl-3-carboxylic acid N-ethylamide), 2-isopropyl-N-2,3-trimethylbutanamide, substituted cyclohexanecarboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl-3,6-di- and -trioxaalkanoates, 3-menthyl methoxyacetate and icilin.

Preferred cooling agents are L-menthol, D-menthol, racemic menthol, menthone glycerol acetal (trade name: Frescolat® MGA), menthyl lactate (preferably L-menthyl lactate, especially L-menthyl L-lactate (trade name: Frescolat® ML)), substituted menthyl-3-carboxamides (e.g. menthyl-3-carboxylic acid N-ethylamide), 2-isopropyl-N-2,3-trimethylbutanamide, substituted cyclohexanecarboxamides, 3-menthoxypropane-1,2-diol, 2-hydroxyethyl menthyl carbonate, 2-hydroxypropyl menthyl carbonate and isopulegol.

Particularly preferred cooling agents are L-menthol, racemic menthol, menthone glycerol acetal (trade name: Frescolat® MGA), menthyl lactate (preferably L-menthyl lactate, especially L-menthyl L-lactate (trade name: Frescolat® ML)), 3-menthoxypropane-1,2-diol, 2-hydroxyethyl menthyl carbonate and 2-hydroxypropyl menthyl carbonate.

Very particularly preferred cooling agents are L-menthol, menthone glycerol acetal (trade name: Frescolat® MGA) and menthyl lactate (preferably L-menthyl lactate, especially L-menthyl L-lactate (trade name: Frescolat® ML)).

Depending on the substance, the use concentration of the cooling agents to be used ranges preferably from 0.01 to 20 wt. % and particularly preferably from 0.1 to 5 wt. %, based on the total weight of the finished (ready-to-use), preferably topical, cosmetic or therapeutic (pharmaceutical) formulation.

The formulations according to the invention can preferably contain (other) skin and hair lightening compounds suitable for cosmetic (e.g. dermatological) and/or therapeutic applications. Advantageous skin and hair lightening compounds in this context are kojic acid (5-hydroxy-2-hydroxymethyl-4-pyranone), kojic acid derivatives, e.g. kojic acid dipalmitate, arbutin, ascorbic acid, ascorbic acid derivatives, hydroquinone, hydroquinone derivatives, resorcinol, sulfur-containing molecules, e.g. glutathione or cysteine, alpha-hydroxy acids (e.g. citric acid, lactic acid, malic acid) and derivatives thereof, N-acetyltyrosine and derivatives, undecenoylphenylalanine, gluconic acid, 4-alkylresorcinols, 4-(1-phenylethyl)-1,3-dihydroxybenzene, chromone derivatives such as aloesin, flavonoids, thymol derivatives, 1-aminoethylphosphinic acid, thiourea derivatives, ellagic acid, nicotinamide (niacinamide), zinc salts, e.g. zinc chloride or gluconate, thujaplicin and derivatives, triterpenes such as maslinic acid, sterols such as ergosterol, benzofuranones such as senkyunolide, vinyl- and ethylguaiacol, dioic acids such as octadecenedioic acid and azelaic acid, inhibitors of nitrogen oxide synthesis, e.g. L-nitroarginine and derivatives thereof, 2,7-dinitroindazole or thiocitrullin, metal chelators (e.g. alpha-hydroxy fatty acids, palmitic acid, phytic acid, lactoferrin, humic acid, gallic acid, bile extracts, bilirubin, biliverdin, EDTA, EGTA and derivatives thereof), retinoids, soya milk and soya extract, serine protease inhibitors or lipoic acid, or other synthetic or natural skin and hair lightening compounds, the latter also being used in the form of a plant extract, e.g. bearberry extract, rice extract, papaya extract, licorice extract or components obtained therefrom by enrichment, such as glabridin or licochalcone A, Artocarpus extract, extracts of *Rumex* and *Ramulus* species, extracts of pine species (*Pinus*) and extracts of *Vitis* species, or stilbene derivatives obtained therefrom by enrichment, and Saxifraga, mulberry, Scutelleria and/or grape extracts.

The amount of the aforementioned exemplary (other) skin and hair lightening compounds (one or more compounds) in the formulations according to the invention is then preferably 0.005 to 30 wt. %, particularly preferably 0.01 to 20 wt. % and very particularly preferably 0.01 to 5 wt. %, based on the total weight of the formulation.

As dyes . . . formulations according to the invention (especially if application to the facial area is intended), it can be advantageous to choose one or more substances from the following group: 2,4-dihydroxyazobenzene, 1-(2'-chloro-4'-nitro-1'-phenylazo)-2-hydroxynaphthalene, ceres red, 2-(4-sulfo-1-naphthylazo)-1-naphthol-4-sulfonic acid, calcium 2-hydroxy-1,2'-azonaphthalene-1'-sulfonate, calcium and barium salts of 1-(2-sulfo-4-methyl-1-phenylazo)-2-naphthylcarboxylic acid, the calcium salt of 1-(2-sulfo-1-naphthylazo)-2-hydroxynaphthalene-3-carboxylic acid, the aluminium salt of 1-(4-sulfo-1-phenylazo)-2-naphthol-6-sulfonic acid, the aluminium salt of 1-(4-sulfo-1-naphthylazo)-2-naphthol-3,6-disulfonic acid, 1-(4-sulfo-1-naphthylazo)-2-naphthol-6,8-disulfonic acid, the aluminium salt of 4-(4-sulfo-1-phenylazo)-1-(4-sulfophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, the aluminium salt of 2,4,5,7-tetraiodofluorescein, the aluminium salt of quinophthalonedisulfonic acid, the aluminium salt of indigodisulfonic acid, red and black iron oxide (Colour Index Number (CIN): 77491 (red) and 77499 (black)), hydrated iron oxide (CIN: 77492), manganese ammonium diphosphate and titanium dioxide.

Other advantageous dyes are oil-soluble natural dyes such as paprika extracts, β-carotene or cochineal.

Dermatological formulations containing pearlescent pigments are also advantageous for the purposes of the present invention. The types of pearlescent pigments listed below are particularly preferred:
1. natural pearlescent pigments such as:
   pearl essence (guanine/hypoxanthine mixed crystals from fish scales) and
   mother of pearl (ground mussel shells)
2. monocrystalline pearlescent pigments such as bismuth oxychloride (BiOCl)
3. sheet pigments, e.g. mica/metal oxide Pearlescent pigments are based e.g. on pulverulent pigments or castor oil dispersions of bismuth oxychloride and/or titanium dioxide and bismuth oxychloride and/or titanium dioxide on mica. The lustre pigment listed under CIN 77163, for example, is particularly advantageous.

Of course, the stated list of pearlescent pigments shall not imply a limitation. Pearlescent pigments which are advantageous for the purposes of the present invention are obtainable by a large number of methods known per se. For example, substrates other than mica, e.g. silica and the like, can also be coated with other metal oxides. For example, $SiO_2$ particles coated with $TiO_2$ and $Fe_2O_3$ ("Ronaspheres"), which are marketed by Merck and are particularly suitable for the optical reduction of fine wrinkles, are advantageous.

Furthermore, it may be advantageous to dispense completely with a substrate like mica. Particular preference is afforded to iron pearlescent pigments which are prepared without using mica. Such pigments are obtainable e.g. under the trade name Sicopearl Kupfer 1000 from BASF.

Effect pigments obtainable in different colours (yellow, red, green, blue) from Flora Tech under the trade name (Metasomes Standard/Glitter are also particularly advantageous. The Glitter particles here take the form of mixtures with various auxiliary substances and dyes (e.g. the dyes of CIN 19140, 77007, 77289, 77491).

The dyes and pigments can be present either individually or in a mixture and can be coated with one another, different colour effects generally being created by different coating thicknesses. The total amount of dyes and coloured pigments is advantageously chosen within the range from e.g. 0.1 wt. % to 30 wt. %, preferably from 0.5 to 15 wt. % and particularly preferably from 1.0 to 10 wt. %, based in each case on the total weight of the (cosmetic) formulations.

The formulations according to the invention can also contain (additional) antioxidants or preservatives. Any antioxidants that are suitable or customary for cosmetic (e.g. dermatological) and/or therapeutic applications can be used as antioxidants or preservatives.

For the purposes of the invention, antioxidants are any substances that lower the quantity of free radicals in cells and tissues. Advantageously, antioxidants are selected from the group comprising amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. alpha-carotene, beta-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, gamma-linoleyl, cholesteryl, glyceryl and oligoglyceryl esters) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa- and heptathionine sulfoximine) in very low acceptable doses (e.g. pmol to µmol/kg), and also (metal) chelators (e.g. alpha-hydroxy fatty acids, palmitic acid, phytic acid, lactoferrin, alpha-hydroxy acids (e.g. citric acid, lactic acid, malic acid), humic acid, gallic acid, bile extracts, tannins, bilirubin, biliverdin, EDTA, EGTA and derivatives thereof), unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glucoside), tocopherols and derivatives (e.g. vitamin E acetate), vitamin A and derivatives (vitamin A palmitate) and coniferyl benzoate from benzoin, rutic acid and derivatives thereof, flavonoids and glycosylated precursors thereof, especially quercetin and derivatives thereof, e.g. alpha-glucosylrutin, rosmaric acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, ursolic acid, levulic acid, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenium methionine), superoxide dismutase, stilbenes and derivatives thereof (e.g. stilbene oxide, trans-stilbene oxide) and the derivatives of said active substances which are suitable according to the invention (salts, esters, ethers, sugars, nucleotides, nucleosides, peptides and lipids), or plant extracts or fractions with an antioxidative effect, e.g. green tea, rooibos, honeybush, grape, rosemary, sage, melissa, thyme, lavender, olive, oats, cacao, ginkgo, ginseng, licorice, honeysuckle, *Sophora, Pueraria, Pinus, Citrus, Phyllanthus emblica* or St John's wort, grape seeds, wheat germ and *Phyllanthus emblica*.

Other suitable antioxidants are coenzymes, e.g. coenzyme Q10, plastoquinone, menaquinone, ubiquinols 1-10, ubiquinones 1-10 or derivatives of these substances.

The amount of antioxidants (one or more compounds) in the formulations according to the invention is preferably 0.01 to 20 wt. %, particularly preferably 0.05 to 10 wt. % and very particularly preferably 0.2 to 5 wt. %, based on the total weight of the formulation.

If the antioxidant(s) consists (consist) of vitamin E and/or derivatives thereof, it is advantageous to choose their respective concentrations from the range 0.001 to 10 wt. %, based on the total weight of the formulation.

If the antioxidant(s) consists (consist) of vitamin A or vitamin A derivatives, or of carotenes or derivatives thereof, it is advantageous to choose their respective concentrations from the range 0.001 to 10 wt. %, based on the total weight of the formulation.

Formulations according to the invention can also contain preservatives. Preservatives which can be used are any antioxidants that are suitable or customary for cosmetic (e.g. dermatological) and/or therapeutic applications, classic preservatives (e.g. formaldehyde, glutaric dialdehyde, parabens (e.g. methyl-, ethyl-, propyl- and butylparaben), dibromodicyanobutane, imidazolidinylureas ("Germall"), isothiazolinones ("Kathon"), methylchlorothiazolidine, methylthiazolidine, organic acids (e.g. benzoic acid, sorbic acid, salicylic acid) and salts and esters thereof, propionic acid and formic acid and salts thereof, glycols, e.g. propylene glycol, and 1,2-dihydroxyalkanes) and plant-based preservation aids, e.g. lantadin A, caryophyllene, hesperidin, diosmin, phellandrene, pigenin, quercetin, hypericin, aucubin, diosgenin, plumbagin, corlilagin, etc.

It can also be advantageous to use anti-irritants in formulations according to the invention, possible anti-irritants being any anti-inflammatory or redness-alleviating and itch-alleviating substances that are suitable or customary for cosmetic (e.g. dermatological) and/or therapeutic applications. Preferred substances are all those which reduce the amount of cytokines, interleukins, prostaglandins and/or leukotrienes in cells and tissues.

The anti-inflammatory or redness-alleviating and itch-alleviating substances used are advantageously steroidal anti-inflammatory substances of the corticosteroid type, e.g. hydrocortisone, dexamethasone, dexamethasone phosphate, methylprednisolone or cortisone, it being possible to extend the list with other steroidal anti-inflammatories. It is also possible to use non-steroidal anti-inflammatories. Examples which should be mentioned here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen or benoxaprofen, or pyrazoles such as phenylbutazone, oxyphenylbutazone, febrazone or azapropazone. A possible alternative is to use natural anti-inflammatory or redness-alleviating and itch-alleviating substances. Plant extracts, special high-activity plant extract fractions and high-purity active substances isolated from plant extracts can be used. Particular preference is afforded to extracts, fractions and active substances from chamomile, Aloe vera, *Commiphora* species, *Rubia* species, *Echinacea* species, willow, willow-herb, oats, black and green tea, gingko, coffee, pepper, currants, tomato, vanilla, almonds, and pure substances such as, inter alia, bisabolol, apigenin-7-glucoside, boswellic acid, phytosterols, glycyrrhizinic acid, glabridin or licochalcone A.

The amount of anti-irritants (one or more compounds) in formulations according to the invention is preferably 0.01 to 20 wt. %, particularly preferably 0.03 to 10 wt. % and very particularly preferably 0.05 to 5 wt. %, based on the total weight of the formulation.

The formulations according to the invention (especially topical cosmetic formulations) can also contain moisture retention regulators and osmolytes. The following substances are examples of moisture retention regulators (moisturizers) used: sodium lactate, urea, alcohols (especially 1,2-pentanediol, 1,2-hexanediol, 1,2-octanediol, 1,2-decanediol and mixtures thereof), sorbitol, glycerol, propylene glycol, collagen, elastin or hyaluronic acid, diacyl adipates, petrolatum, ectoin, urocanic acid, lecithin, pantheol, phytantriol, lycopene, algal extract, ceramides, cholesterol, glycolipids, chitosan, chondroitin sulfate, polyamino acids and polyamino sugars, lanolin, lanolin esters, amino acids, alpha-hydroxy acids (e.g. citric acid, lactic acid, malic acid) and derivatives thereof, sugars (e.g. inositol), alpha-hydroxy fatty acids, phytosterols, triterpene acids such as betulinic acid or ursolic acid, and algal extracts. Examples of osmolytes which can be used are sugar alcohols (myoinositol, mannitol, sorbitol), quaternary amines such as taurine, choline, betaine, betaine glycine, ectoin, diglycerol phosphate, phosphorylcholine, glycerophosphorylcholines, amino acids such as glutamine, glycine, alanine, glutamate, aspartate or proline, phosphatidylcholine, phosphatidylinositol, inorganic phosphates, and polymers of said compounds, such as proteins, peptides, polyamino acids and polyols.

The formulations according to the invention (e.g. topical cosmetic formulations) also advantageously contain antimicrobial substances. The following may be mentioned as examples:

Fatty alcohols, aldehydes and acids having chain lengths of $C_2$ to $C_{40}$ which are aryl- or aryloxy-substituted, unbranched or monoalkyl- and polyalkyl-branched and saturated or monounsaturated to pentaunsaturated (up to five double or triple bonds, including mixed ene/yne compounds).

Alkanediols, dialdehydes and dicarboxylic acids having chain lengths of $C_2$ to $C_{40}$, particularly preferably of $C_4$ to $C_{12}$, which are aryl- or aryloxy-substituted, unbranched or monoalkyl- and polyalkyl-branched and saturated or monounsaturated to pentaunsaturated (up to five double or triple bonds, including mixed ene/yne compounds).

Mono- and oligoglycerides (up to 4 glycerol units) of fatty alcohols (mono- and oligoglycerol monoalkyl ethers), fatty acids (mono- and oligoglycerol monoalkyl esters), alkanediols (mono- and oligoglycerol monoalkyl ethers; bis (mono-/oligoglyceryl)alkyl diethers) and dicarboxylic acids (mono- and oligoglycerol monoalkyl esters; bis(mono-/oligoglyceryl)alkyl diesters) having chain lengths of $C_2$ to $C_{40}$ which are aryl- or aryloxy-substituted, unbranched or monoalkyl- and polyalkyl-branched and saturated or monounsaturated to pentaunsaturated (up to five double or triple bonds, including mixed ene/yne compounds).

Fatty acid esters of carboxylic acids having chain lengths of $C_2$ to $C_{40}$ which are unbranched or monoalkyl- and polyalkyl-branched, saturated or monounsaturated to pentaunsaturated (up to five double or triple bonds, including mixed ene/yne compounds) and optionally also aryl- or aryloxy-substituted, with monohydric to hexahydric fatty alcohols having chain lengths of $C_2$ to $C_{40}$ which are unbranched or monoalkyl- and polyalkyl-branched, saturated or monounsaturated to pentaunsaturated (up to five double or triple bonds, including mixed ene/yne compounds) and optionally also aryl- or aryloxy-substituted.

Vegetable and animal fatty acid cuts containing fatty alcohols, aldehydes and acids having chain lengths of $C_2$ to $C_{40}$ which are unbranched or monoalkyl- and polyalkyl-branched and saturated or monounsaturated to pentaunsaturated (up to five double or triple bonds, including mixed ene/yne compounds) (e.g. coconut fatty acids, palm kernel fatty acids, wool wax acids).

Mono- and oligoglycerides of lanolin, lanolin alcohols and lanolin acids (e.g. glyceryl lanolate, neocerite), glycyrrhetinic acid and derivatives (e.g. glycyrrhetinyl stearates), natural and synthetic cardenolides (e.g. digitoxin, digoxin, digoxygenin, gitoxygenin, strophanthin and strophanthidin), natural and synthetic bufadienolides (e.g. scillaren A, scillarenin and bufotalin), sapogenins and steroid sapogenins (e.g. amyrins, oleanolic acid, digitonin, gitogenin, tigogenin and diosgenin), and steroid alkaloids of vegetable and animal origin (e.g. tomatidine, solanine, solanidine, conessine, batrachotoxin and homobatrachotoxin).

Monohalogenated and polyhalogenated nitriles, dinitriles, trinitriles or tetranitriles.

Mono- and oligohydroxy fatty acids having chain lengths of $C_2$ to $C_{24}$ (e.g. lactic acid, 2-hydroxypalmitic acid), oligomers and/or polymers thereof and vegetable and animal raw materials containing them.

Acyclic terpenes: terpene hydrocarbons (e.g. ocimene, myrcene), terpene alcohols (e.g. geraniol, linalool, citronellol), terpene aldehydes and ketones (e.g. citral, pseudoionone, beta-ionone); monocyclic terpenes: terpene hydrocarbons (e.g. terpinene, terpinolene, limonene), terpene alcohols (e.g. terpineol, thymol, menthol), terpene ketones (e.g. pulegone, carvone); bicyclic terpenes: terpene hydrocarbons (e.g. carane, pinane, bornane), terpene alcohols (e.g. borneol, isoborneol), terpene ketones (e.g. camphor); sesquiterpenes: acyclic sesquiterpenes (e.g. farnesol, nerolidol), monocyclic sesquiterpenes (e.g. bisabolol), bicyclic sesquiterpenes (e.g. cardinene, selinene, vetivazulene, guaiazulene), tricyclic sesquiterpenes (e.g. santalene), diterpenes (e.g. phytol), tricyclic diterpenes (e.g. abietic acid), triterpenes (squalenoids, e.g. squalene), tetraterpenes.

Ethoxylated, propoxylated or mixed ethoxylated/propoxylated cosmetic fatty alcohols, fatty acids and fatty acid esters having chain lengths of $C_2$ to $C_{40}$ and 1 to 150 EO and/or PO units.

Antimicrobial peptides and proteins having an amino acid number of 4 to 200, e.g. skin antimicrobial peptides (SAPs), lingual antimicrobial peptides (LAPs), human beta-defensins (especially h-BD1 and h-BD2), lactoferrins and hydrolysates thereof, as well as peptides obtained therefrom, bactericidal/permeability-increasing proteins (BPIs), cationic microbial proteins (CAPs), lysozyme.

Suitable carbohydrates or "carbohydrate derivatives", which will also be abbreviated to "carbohydrates", are sugars and substituted sugars or compounds containing sugar residues. The sugars include especially the deoxy and dideoxy forms, N-acetylgalactosamine-, N-acetylglucosamine- and sialic acid-substituted derivatives, and sugar esters and ethers. The following are preferred:

a) monosaccharides, particularly including pentoses and hexoses,
b) disaccharides, particularly including sucrose, maltose and lactobiose,
c) oligosaccharides, particularly including trisaccharides and tetrasaccharides, and
d) polysaccharides, particularly including starch, glycogen, cellulose, dextran, tunicin, inulin, chitin, especially chitosans, chitin hydrolysates, alginic acid and alginates, plant gums, mucus, pectins, mannans, galactans, xylans, araban, polyoses, chondroitin sulfates, heparin, hyaluronic acid and glycosaminoglycans, hemicelluloses, substituted cellulose and substituted starch, especially the respective hydroxyalkyl-substituted polysaccharides.

Amylose, amylopectin, xanthan and alpha-, beta- and gamma-dextrin are particularly suitable. The polysaccharides can consist of e.g. 4 to 1,000,000 and especially 10 to 100,000 monosaccharides. The chain lengths chosen in each case are preferably such as to ensure that the active substance is soluble in or can be incorporated into the formulation in question.

Sphingolipids such as sphingosine; N-monoalkylated sphingosines; N,N-dialkylated sphingosines; sphingosine-1-phosphate; sphingosine-1-sulfate; psychosine (sphingosine beta-D-galactopyranoside); sphingosylphosphorylcholine; lysosulfatides (sphingosyl galactosylsulfate; lysocerebroside sulfate); lecithin; sphingomyelin; sphinganin.

It is also possible to use so-called "natural" antibacterial substances, most of which are ethereal oils. Examples of typical oils with an antibacterial action are oils from anise, lemon, orange, rosemary, wintergreen, clove, thyme, lavender, hops, citronella, wheat, lemongrass, cedarwood, cinnamon, geranium, sandalwood, violet, eucalyptus, peppermint, gum benzoin, basil, fennel, menthol and *Ocmea origanum, Hydastis carradensis, Berberidaceae daceae, Ratanhiae* or *Curcuma longa.*

Important substances with an antimicrobial action which can be found in ethereal oils are e.g. anethole, catechol, camphene, carvacrol, eugenol, eucalyptol, ferulic acid, farnesol, hinokitiol, tropolone, limonene, menthol, methyl salicylate, thymol, terpineol, verbenone, berberine, curcumin, caryophyllene oxide, nerolodol and geraniol.

It is also possible to use mixtures of said active systems or active substances, as well as combinations containing these active substances.

The amount of antimicrobial substances in the formulations is preferably 0.01 to 20 wt. % and particularly preferably 0.05 to 10 wt. %, based on the total weight of the formulations.

The formulations according to the invention (especially cosmetic formulations, including dermatological formulations) can contain deodorants, i.e. substances with a deodorizing and antiperspirant action. These include e.g. odour masking agents such as the common perfume constituents, antiperspirants based on aluminium, zirconium or zinc salts, odour absorbers, e.g. the sheet silicates described in German Offenlegungsschrift DE-P 40 09 347, including particularly montmorillonite, kaolinite, nontronite, saponite, hectorite, bentonite and smectite, and also e.g. zinc salts of ricinoleic acid. They also include bactericidal or bacteriostatic deodorizing substances, e.g. hexachlorophene, 2,4,4'-trichloro-2'-hydroxydiphenyl ether (Irgasan), 1,6-di(4-chlorophenylbiguanido)hexane (chlorhexidine), 3,4,4'-trichlorocarbanilide, and the active agents described in German Offenlegungsschriften DE-37 40 186, DE-39 38 140, DE-42 04 321, DE-42 29 707, DE-42 29 737, DE-42 37 081, DE-43 09 372 and DE-43 24 219, and contain cationic substances such as quaternary ammonium salts and odour absorbers, e.g. Grillocin® (combination of zinc ricinoleate and various additives) or triethyl citrate, optionally in combination with ion exchange resins.

The amount of deodorizing and/or antiperspirant substances in the formulations is preferably 0.01 to 20 wt. % and particularly preferably 0.05 to 10 wt. %, based on the total weight of the formulations.

The formulations according to the invention (especially cosmetic formulations) can also contain anionic, cationic, non-ionic and/or amphoteric surfactants, especially if crystalline or microcrystalline solids, e.g. inorganic micropigments, are to be incorporated into the formulations.

Anionic surfactants normally contain carboxylate, sulfate or sulfonate groups as functional groups. In aqueous solution they form negatively charged organic ions in an acidic or neutral medium. Cationic surfactants are characterized virtually exclusively by the presence of a quaternary ammonium group. In aqueous solution they form positively charged organic ions in an acidic or neutral medium. Amphoteric surfactants contain both anionic and cationic groups and accordingly behave like anionic or cationic surfactants in aqueous solution, depending on the pH. They have a positive charge in a strongly acidic medium and a negative charge in an alkaline medium. In the neutral pH range, on the other hand, they are zwitterionic. Polyether chains are typical of non-ionic surfactants. Non-ionic surfactants do not form ions in an aqueous medium.

A. Anionic Surfactants

Anionic surfactants that can advantageously be used are acylamino acids (and salts thereof) such as acylglutamates, e.g. sodium acylglutamate, di-TEA palmitoylaspartate and sodium caprylic/capric glutamate, acylpeptides, e.g. palmitoyl-hydrolysed lactoprotein, sodium cocoyl-hydrolysed soya protein and sodium/potassium cocoyl-hydrolysed collagen, sarcosinates, e.g. myristoyl sarcosine, TEA lauroylsarcosinate, sodium lauroylsarcosinate and sodium cocoylsarcosinate, taurates, e.g. sodium lauroyltaurate and sodium methylcocoyltaurate, acyllactylates, lauroyllactylate and caproyllactylate, alaninates;

carboxylic acids and derivatives, such as lauric acid, aluminium stearate, magnesium alkanolate and zinc undecylenate, ester-carboxylic acids, e.g. calcium stearoyllactylate, laureth-6 citrate and sodium PEG-4 lauramidocarboxylate, ether-carboxylic acids, e.g. sodium laureth-13 carboxylate and sodium PEG-6 cocamidocarboxylate;

phosphoric acid esters and salts, such as DEA oleth-10 phosphate, dilaureth-4 phosphate and cetyl phosphate derivatives (e.g. those described in WO 2004/075868);

sulfonic acids and salts, such as acylisethionates, e.g. sodium/ammonium cocoylisethionate, alkylarylsulfonates, alkylsulfonates, e.g. sodium coco monoglyceridesulfate, sodium $C_{12-14}$-olefinsulfonate, sodium laurylsulfoacetate and magnesium PEG-3 cocamidosulfate, sulfosuccinates, e.g. sodium dioctylsulfosuccinate, disodium laureth sulfosuccinate, disodium laurylsulfosuccinate and disodium MEA undecylenamidosulfosuccinate;

and sulfuric acid esters such as alkyl ether sulfate, e.g. sodium, ammonium, magnesium, MIPA and TIPA laureth sulfate, sodium myreth sulfate and sodium C12-13 pareth sulfate, alkylsulfates, e.g. sodium, ammonium and TEA laurylsulfate.

B. Cationic Surfactants

Cationic surfactants that can advantageously be used are alkylamines, alkylimidazoles, ethoxylated amines and quaternary surfactants:

$RNH_2CH_2CH_2COO^-$ (at pH 7)

$RNHCH_2CH_2COO^-B^+$ (at pH 12), $B^+$=arbitrary cation, e.g. $Na^+$ esterquats Quaternary surfactants contain at least one N atom that is covalently bonded to 4 alkyl or aryl groups. This produces a positive charge, irrespective of the pH. Alkylbetaine, alkylamidopropylbetaine and alkylamidopropylhydroxysulfaine are advantageous. The cationic surfactants used can also preferably be selected from the group comprising quaternary ammonium compounds, in particular benzyltrialkylammonium chlorides or bromides, e.g. benzyldimethylstearylammonium chloride, and also alkyltrialkylammonium salts, e.g. cetyltrimethylammonium chloride or bromide, alkyldimethylhydroxyethylammonium chlorides or bromides, dialkyldimethylammonium chlorides or bromides, alkylamidoethyltrimethylammonium ether sulfates, alkylpyridinium salts, e.g. lauryl- or cetylpyrimidinium chloride, imidazoline derivatives and compounds of a cationic nature, such as amine oxides, e.g. alkyldimethylamine oxides or alkylaminoethyldimethylamine oxides. Cetyltrimethylammonium salts can be used particularly advantageously.

C. Amphoteric Surfactants

Amphoteric surfactants that can advantageously be used are acyl-/dialkylethylenediamine, e.g. sodium acylamphoacetate, disodium acylamphodipropionate, disodium alkylamphodiacetate, sodium acylamphohydroxypropylsulfonate, disodium acylamphodiacetate and sodium acylamphopropionate, N-alkylamino acids, e.g. aminopropylalkylglutamide, alkylaminopropionic acid, sodium alkylimidodipropionate and lauroamphocarboxyglycinate.

D. Non-ionic Surfactants

Non-ionic surfactants that can advantageously be used are
alcohols,
alkanolamides such as cocamides MEA/DEA/MIPA,
amine oxides such as cocamidopropylamine oxide,
esters formed by the esterification of carboxylic acids with ethylene oxide, glycerol, sorbitan or other alcohols,
ethers, e.g. ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers, and alkyl polyglycosides such as lauryl glucoside, decyl glycoside and coco glycoside,
sucrose esters and ethers,
polyglycerol esters, diglycerol esters and monoglycerol esters,
methyl glucose esters and esters of hydroxy acids.

The use of a combination of anionic and/or amphoteric surfactants with one or more non-ionic surfactants is also advantageous.

The surface-active substance (surfactant) or the combination of surface-active substances can be present in a concentration of between 1 and 98 wt. % in the formulations according to the invention, based on the total weight of the formulations.

Cosmetic (e.g. dermatological) or therapeutic formulations according to the invention, containing the compounds of formula (I) according to the invention or to be used according to the invention, can also take the form of emulsions.

The oily phase (lipid phase) in the formulations according to the invention (especially topical cosmetic formulations) can advantageously be selected from the following group of substances:

mineral oils (advantageously paraffin oil) and mineral waxes;
fatty oils, fats, waxes and other natural and synthetic fatty substances, preferably esters of fatty acids with alcohols of low C number, e.g. with isopropanol, propylene glycol or glycerol, or esters of fatty alcohols with alkanoic acids of low C number or with fatty acids;
alkyl benzoates (e.g. mixtures of n-dodecyl, n-tridecyl, n-tetradecyl or n-pentadecyl benzoate);
cyclic or linear silicone oils such as dimethylpolysiloxanes, diethylpolysiloxanes, diphenylpolysiloxanes and mixed forms thereof.

It is advantageous to use (natural or synthetic) esters, especially (a) esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, and (b) esters of aromatic carboxylic acids and saturated and/or unsaturated, branched and/or unbranched alcohols having a chain length of 3 to 30 C atoms. Preferred ester oils are isopropyl myristate, isopropyl palmitate, isopropyl stearate, isopropyl oleate, n-butyl stearate, n-hexyl laurate, n-decyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, cetearyl 2-ethylhexanoate, 2-ethylhexyl palmitate, 2-ethylhexyl laurate, 2-hexyldecyl stearate, 2-octyldecyl palmitate, 2-octyldodecyl palmitate, oleyl oleate, oleyl erucate, erucyl oleate, erucyl erucate, di-2-ethylhexyl 2,6-naphthalenedioate and synthetic, semisynthetic and natural mixtures of such esters, e.g. jojoba oil.

Furthermore, the oily phase can advantageously be selected from the group comprising branched and unbranched hydrocarbons and waxes, silicone oils, dialkyl ethers, the group comprising saturated or unsaturated, branched or unbranched alcohols, and also fatty acid triglycerides, specifically the triglycerol esters of saturated and/or unsaturated, branched and/or unbranched alkane-carboxylic acids having a chain length of 8 to 24 and especially 12 to 18 C atoms. The fatty acid triglycerides can advantageously be selected from the group comprising synthetic, semisynthetic and natural oils, e.g. triglycerides of capric or caprylic acid, apricot kernel oil, avocado oil, cottonseed oil, borage seed oil, thistle oil, groundnut oil, gamma-oryzanol, rose-hip oil, hemp oil, hazelnut oil, currant seed oil, coconut oil, cherry kernel oil, salmon oil, linseed oil, maize oil, macadamia nut oil, almond oil, evening primrose oil, mink oil, olive oil, palm oil, palm kernel oil, pecan nut oil, peach kernel oil, pistachio nut oil, rapeseed oil, rice germ oil, castor oil, safflower oil, sesame oil, soya oil, sunflower oil, tea tree oil, grapeseed oil or wheatgerm oil and the like. Arbitrary mixtures of such oil and wax components can also advantageously be used. In some cases it is also advantageous to use waxes, e.g. cetyl palmitate, as the sole lipid component of the oily phase; advantageously, the oily phase is selected from the group comprising 2-ethylhexyl isostearate, octyldodecanol, isotridecyl isononanoate, isoeicosane, 2-ethylhexyl cocoate, $C_{12-15}$-alkyl benzoate, caprylic/capric tri-glyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl iso-nonanoate are particularly advantageous. The hydrocarbons paraffin oil, squalane and squalene can also advantageously be used. Advantageously, the oily phase can further contain cyclic or linear silicone oils or consist entirely of such oils, although it is preferable to use other oily phase components in addition to the silicone oil(s). Cyclomethicone (e.g. decamethylcyclopentasiloxane) can advantageously be used as a silicone oil. However, other silicone oils can also advantageously be used, examples being undecamethylcyclotrisiloxane, poly-dimethylsiloxane and poly(methylphenylsiloxane). Furthermore, mixtures of cyclomethicone and isotridecyl isononanoate and of cyclomethicone and 2-ethylhexyl isostearate are particularly advantageous.

The aqueous phase of formulations according to the invention (especially topical cosmetic formulations) that take the form of an emulsion can advantageously comprise alcohols, diols or polyols of low C number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low C number, e.g. ethanol, isopropanol, 1,2-propanediol and glycerol, and in particular one or more thickeners, which can advantageously be selected from the group comprising silicon dioxide, aluminium silicates such as bentonites, polysaccharides or derivatives thereof, e.g. hyaluronic acid, guar kernel flour, xanthan gum, hydroxy-propyl methyl cellulose or allulose derivatives, and particularly advantageously from the group comprising polyacrylates, preferably a polyacrylate from the group comprising the so-called carbopols, e.g. carbopols of types 980, 981, 1382, 2984 and 5984, in each case on their own or in combination, or from the group comprising polyurethanes, and also alpha- or beta-hydroxy acids, preferably lactic acid, citric acid or salicylic acid, as well as emulsifiers, which can advantageously be selected from the group comprising ionic, non-ionic, polymeric, phosphate-containing and zwitterionic emulsifiers.

Formulations according to the invention that take the form of an emulsion advantageously comprise one or more emulsifiers. O/W emulsifiers can, for example, advantageously be selected from the group comprising polyethoxylated or polypropoxylated or polyethoxylated and polypropoxylated products, e.g.:

fatty alcohol ethoxylates,
ethoxylated wool wax alcohols,
polyethylene glycol ethers of the general formula $$R-O-(-CH_2-CH_2-O-)_n-R',$$

fatty acid ethoxylates of the general formula $$R-COO-(-CH_2-CH_2-O-)_n-H,$$

etherified fatty acid ethoxylates of the general formula $$R-COO-(-CH_2-CH_2-O-)_n-R',$$

esterified fatty acid ethoxylates of the general formula $$R-COO-(-CH_2-CH_2-O-)_n-C(O)-R',$$

polyethylene glycol glycerol fatty acid esters,
ethoxylated sorbitan esters,
cholesterol ethoxylates,
ethoxylated triglycerides,
alkyl ether carboxylic acids of the general formula $$R-COO-(-CH_2-CH_2-O-)_n-OOH, \text{ where n is a number from 5 to 30,}$$

polyoxyethylene sorbitol fatty acid esters,
alkyl ether sulfates of the general formula $$R-O-(-CH_2-CH_2-O-)_n-SO_3-H,$$

fatty alcohol propoxylates of the general formula $$R-O-(-CH_2-CH(CH_3)-O-)_n-H,$$

polypropylene glycol ethers of the general formula $$R-O-(-CH_2-CH(CH_3)-O-)_n-R',$$

propoxylated wool wax alcohols,
etherified fatty acid propoxylates $$R-COO-(-CH_2-CH(CH_3)-O-)_n-R',$$

esterified fatty acid propoxylates of the general formula $$R-COO-(-CH_2-CH(CH_3)-O-)_n-C(O)-R',$$

fatty acid propoxylates of the general formula $$R-COO-(-CH_2-CH(CH_3)-O-)_n-H,$$

polypropylene glycol glycerol fatty acid esters,
propoxylated sorbitan esters,
cholesterol propoxylates,
propoxylated triglycerides,
alkyl ether carboxylic acids of the general formula $$R-O-(-CH_2-CH(CH_3)-O-)_n-CH_2-COOH,$$

alkyl ether sulfates, or the acids on which these sulfates are based, of the general formula $$R-O-(-CH_2-CH(CH_3)-O-)_n-SO_3-H,$$

fatty alcohol ethoxylates/propoxylates of the general formula $$R-O-X_n-Y_m-H,$$

polypropylene glycol ethers of the general formula $$R-O-X_n-Y_m-R',$$

etherified fatty acid propoxylates of the general formula $$R-COO-X_n-Y_m-R',$$

fatty acid ethoxylates/propoxylates of the general formula $$R-COO-X_n-Y_m-H.$$

According to the invention, the polyethoxylated or polypropoxylated or polyethoxylated and polypropoxylated O/W emulsifiers used are particularly advantageously selected from the group comprising substances having HLB values of 11 to 18 and very particularly advantageously having HLB values of 14.5 to 15.5, if the O/W emulsifiers contain saturated radicals R and R'. If the O/W emulsifiers contain unsaturated radicals R and/or R', or if isoalkyl derivatives are present, the preferred HLB value of such emulsifiers can also be lower or higher.

It is advantageous to select the fatty alcohol ethoxylates from the group comprising ethoxylated stearyl alcohols, cetyl alcohols and cetylstearyl alcohols (cetearyl alcohols). The following are particularly preferred:

polyethylene glycol (n) stearyl ethers (steareth-n) where n=13-20,
polyethylene glycol (n) cetyl ethers (ceteth-n) where n=13-20,
polyethylene glycol (n) isocetyl ethers (isoceteth-n) where n=13-20,
polyethylene glycol (n) cetylstearyl ethers (ceteareth-n) where n=13-20,
polyethylene glycol (m) isostearyl ethers (isosteareth-m) where m=12-20,
polyethylene glycol (k) oleyl ethers (oleth-k) where k=12-15,
polyethylene glycol (12) lauryl ether (laureth-12),
polyethylene glycol (12) isolauryl ether (isolaureth-12).

It is also advantageous to select the fatty acid ethoxylates from the following group:
polyethylene glycol (n) stearates where n=20-25,
polyethylene glycol (m) isostearates where m=12-25,
polyethylene glycol (k) oleates where k=12-20.

Sodium laureth-11 carboxylate can advantageously be used as an ethoxylated alkyl ether carboxylic acid or a salt thereof. Sodium laureth 1-4 sulfate can advantageously be used as an alkyl ether sulfate. Polyethylene glycol (30) cholesteryl ether can advantageously be used as an ethoxylated cholesterol derivative. Polyethylene glycol (25) soyasterol has also proved useful.

Polyethylene glycol (60) evening primrose glycerides can advantageously be used as ethoxylated triglycerides.

It is also advantageous to select the polyethylene glycol glycerol fatty acid esters from the group comprising polyethylene glycol (n) glyceryl laurates where n=20-23, polyethylene glycol (6) glyceryl caprylate/caprate, polyethylene glycol (20) glyceryl oleate, polyethylene glycol (20) glyceryl isostearate and polyethylene glycol (18) glyceryl oleate/cocoate.

It is likewise favourable to select the sorbitan esters from the group comprising polyethylene glycol (20) sorbitan monolaurate, polyethylene glycol (20) sorbitan monostearate, polyethylene glycol (20) sorbitan monoisostearate, polyethylene glycol (20) sorbitan monopalmitate and polyethylene glycol (20) sorbitan monooleate.

The following can be used as advantageous W/O emulsifiers: fatty alcohols having 8 to 30 carbon atoms, monoglycerol esters of saturated and/or unsaturated, branched and/or unbranched alkanecarboxylic acids having a chain length of 8 to 24 C atoms, especially 12 to 18 C atoms, diglycerol esters of saturated and/or unsaturated, branched and/or unbranched alkanecarboxylic acids having a chain length of 8 to 24 C atoms, especially 12 to 18 C atoms, monoglycerol ethers of saturated and/or unsaturated, branched and/or unbranched alcohols having a chain length of 8 to 24 C atoms, especially 12 to 18 C atoms, diglycerol ethers of saturated and/or unsaturated, branched and/or unbranched alcohols having a chain length of 8 to 24 C atoms, especially 12 to 18 C atoms, propylene glycol esters of saturated and/or unsaturated, branched and/or unbranched alkanecarboxylic acids having a chain length of 8 to 24 C atoms, especially 12 to 18 C atoms, and sorbitan esters of saturated and/or unsaturated, branched and/or unbranched alkanecarboxylic acids having a chain length of 8 to 24 C atoms, especially 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprate and glyceryl monocaprylate.

It is also possible to use mixtures of said active systems.

The total amount of compounds of formula (I), UV absorbers and (other) skin-lightening substances in the formulations according to the invention is preferably 0.01 to 20 wt. % and particularly preferably 0.05 to 15 wt. %, based on the total weight of the formulation.

For use, the topical formulations according to the invention, especially formulations for lightening the skin and hair, are applied to the skin and/or hair in a sufficient amount and in a manner customary for cosmetic preparations.

Other preferred mixtures, especially cosmetic or pharmaceutical formulations, are those which contain the following in a synergistically active amount: one or more UVB and/or UVA filters, one or more antioxidants, one or more skin lighteners or mixtures of two or more of these substances, (a) for reducing or preventing a translocation of the AhR into a cell nucleus, (b) for reducing or preventing a UVB-induced gene expression, (c) for reducing or preventing a gene expression induced or inducible by polycyclic aromatic hydrocarbons, preferably TCDD, and/or (d) for reducing or preventing UVB-induced or UVB-inducible skin damage, especially skin cancer, skin ageing, skin inflammations and sunburn, or for boosting UV protection or lightening the skin.

The invention is described in greater detail below with the aid of the Examples, which are not intended to limit the extent of protection defined by the claims. Unless indicated otherwise, all the data are by weight. The indanones used to prepare the compounds of formulae (Ia), (Ib), (Ic) and (Id) according to the invention can be . . . analogously to in DE 100 55 940.

EXAMPLE 1

Compounds (Ia)

11 g (0.17 mol) of solid potassium hydroxide are suspended in 100 g of diethylene glycol dimethyl ether, and 89 g (0.40 mol) of 3,3-dimethyl-5,6-dimethoxy-1-indanone are added. After heating to 80° C., 65 g (0.60 mol) of benzaldehyde are metered in over one hour and the mixture is stirred for a further 3 h at said temperature. It is cooled to RT, added to 400 g of ice-water and rendered neutral with 30 g of 10% hydrochloric acid. After extraction with 400 g of methyl tert-butyl ether, the product is recrystallized from methanol. Yield: 76% of theory (E/Z mixture). Pure (E) isomer could be isolated by repeated recrystallization.

EXAMPLE 2

Compounds (Ib)

Analogously to Example 1 using 3,3-dimethyl-1-indanone and 3,4-dimethoxybenzaldehyde as starting materials. Yield: 50% of theory (E/Z mixture).

EXAMPLE 3

Compounds (Ic)

Analogously to Example 1 using 3,3-dimethyl-1-indanone and anisaldehyde as starting materials. Yield: 50% of theory (E/Z mixture).

EXAMPLE 4

Compounds (Id)

Analogously to Example 1 using 3,3,6-trimethyl-5-butoxy-1-indanone and anisaldehyde as starting materials. Yield: 70% of theory (E/Z mixture).

EXAMPLE 5

Cell Culture and Irradiation

HaCaT keratinocytes were cultivated in DMEM containing 10% of foetal calf serum. The cells were irradiated with UVB in PBS (phosphate buffered saline). For irradiation with UVB we used a TL20W/12RS lamp, which contains four parallel tubes (Philips, Eindhoven, The Netherlands) and emits the bulk of its energy in the UVB range (290-320 nm). The emission peak of the lamp is at 310 nm. Control cells were subjected to the same treatment but were not irradiated. To inhibit the AhR, the cells were treated with the test substances 1 h prior to irradiation.

Transfection of HaCaT Cells with Plasmid pEGFP-AhR

HaCaT cells were plated out on compartmentalized microscope slides at a cell density of $5\times10^4$ cells/compartment. Some were pretreated for 1 h with the test substances. After 24 h these were transfected with plasmid pEGFP-AhR by means of the FuGene 6 transfection reagent (Roche, Mannheim, Germany) according to the manufacturer's instructions. After a further 24 h the transfected cells were irradiated with 100 $J/m^2$ of UVB. After 40 min the cells were fixed for 10 min with 4% paraformaldehyde and washed with PBS. The slides were dried and covered with Vectashield mounting medium (Vector Laboratories, Burlingame, Calif., USA). The GFP-coupled AhR was visualized by means of a fluorescence microscope (Olympus, Hamburg, Germany) and photographed with a ColorView XS digital camera (Olympus).

RNA Preparation, cDNA Synthesis and Real Time RT-PCR

HaCaT cells were irradiated with 100 $J/m^2$ of UVB. Some cells were pretreated with the test substances 1 h prior to irradiation. After 4 h the RNA was prepared with an RNeasy kit (Qiagen, Hilden, Germany) according to the manufacturer's instructions. Reverse transcription was carried out as described (*Arch. Toxicol.* (2005) PMID 16205913). PCR fragments were amplified by means of real-time PCR in a LightCycler (Roche, Mannheim, Germany). The PCR mix was composed of 1/10 by volume of QuantiTect® SYBR Green PCR Master Mix (Qiagen, Hilden, Germany), 0.5 µmol/l of the appropriate primer, 2 µl of cDNA and DEPC-treated (diethyl pyrocarbonate-treated) $H_2O$ in a final volume of 20 µl. The PCR began by heating for 15 minutes at 95° C. to activate the DNA polymerase. The PCR conditions were as follows: 40 cycles of 15 sec at 94° C. for denaturing, 25 sec at 60° C. for primer attachment, 30 sec at 72° C. for extension and 2 sec at 72° C. for fluorescence measurement. PCR primers for human CYP1A1 had the following sequences: 5'-TAGACACTGATCTGGCTGCAG for the forwards primer and 5'-GGGAAGGCTCCATCAGCATC for the reverse primer (Cancer Res. 1990, 50, 4315), which formed a 146 bp fragment after amplification. The PCR products were quantified via a fragment-specific standard curve using Light-Cycler software 3. Standard curves were established with $10^2$ to $10^6$ CYP1A1 cDNA copies/µl and amplified as described above.

Results

1) Fluorescence Microscopy

The standard 3-methoxy-4-nitroflavone inhibited the translocation of the AhR into the cell nucleus in the presence and absence of UVB light, thereby exhibiting the action expected according to the literature.

2) Quantification of AhR Inhibition Via Determination of CYP1A1-mRNA

TABLE 1

| Substance | Concentration | CYP1A1 inhibition in the presence of UVB light* | CYP1A1 inhibition in the absence of UVB light** |
|---|---|---|---|
| (Ia) | 32 µM | 97% | 94% |
| (Ib) | 32 µM | 65% | 61% |

*relative to the control (PBS without test substances, containing 0.1% of DMSO, irradiated with UVB)
**relative to the control (PBS without test substances, containing 0.1% of DMSO, not irradiated)

The compounds of formulae (Ia) and (Ib) inhibited the induction of CYP1A1 as a result of AhR activation in the presence and absence of UVB light.

Light Stability Test

Procedure

20 µl of a 1-3 wt. % solution of each of the test compounds of formula (I) in a low-volatility solvent (e.g. isopropyl myristate, miglyol or glycerol) are distributed uniformly over microscope slides using a pipette. These loaded slides are then irradiated in a solar simulator with an intensity of 40 $W/m^2$ (for 2 h or 4 h in each case).

When the irradiation has ended, the slides are each separately laid in a glass dish containing an organic solvent (methanol, isopropanol, etc.) and the organic substances present thereon are detached in an ultrasonic bath. The resulting solutions are each transferred to a 10 ml or 25 ml volumetric flask and made up to the calibration mark with solvent. Non-irradiated slides are treated likewise as references.

Evaluation

The samples (contents of the respective volumetric flasks) are evaluated via HPLC quantification. These values are compared with the non-irradiated references and the degradation rate during irradiation is reported in [wt. %] per unit time, based on the sum [E isomer+Z isomer].

EXAMPLES

| Substance | Degradation after 2 h | Degradation after 4 h |
|---|---|---|
| Vitamin A acid | 95% | 100% |
| Resveratrol (E/Z mixture) | 77% | 84% |
| (Ia) (E/Z mixture) | 7% | 7% |
| (Ib) (E/Z mixture) | 4% | 15% |
| (Ic) (E/Z mixture) | 1% | 1% |
| (Id) (E/Z mixture) | 7% | 11% |

EXAMPLE 6

Depigmenting Action

Figure 1:
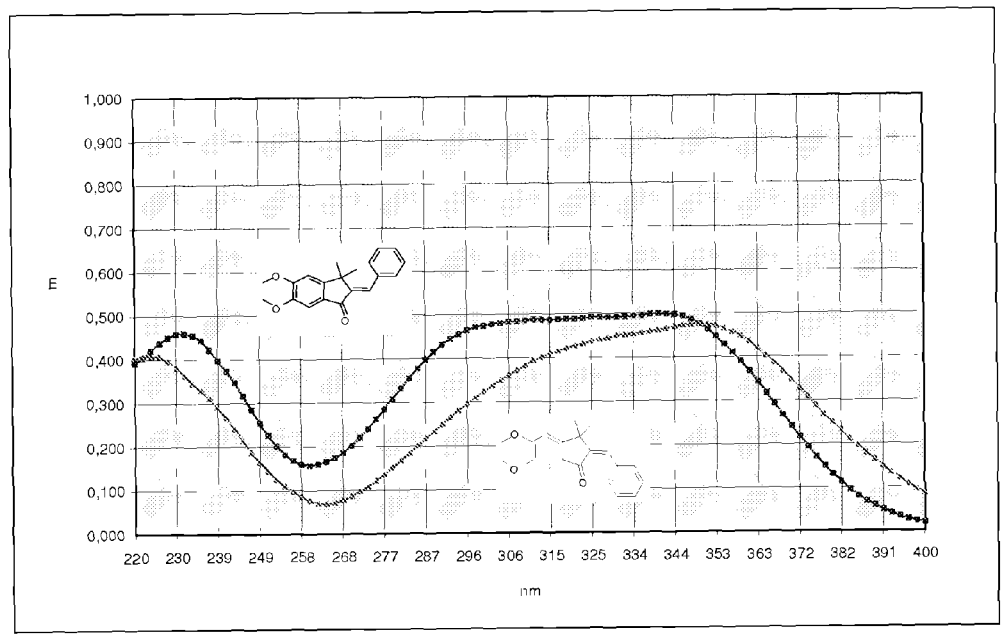
FIG. 1 shows the UV absorption spectra of each of the compounds (Ia) separately in the form of the (E) or (Z) isomer (1% solution in ethanol, 1 cm path length).
Figure 2:
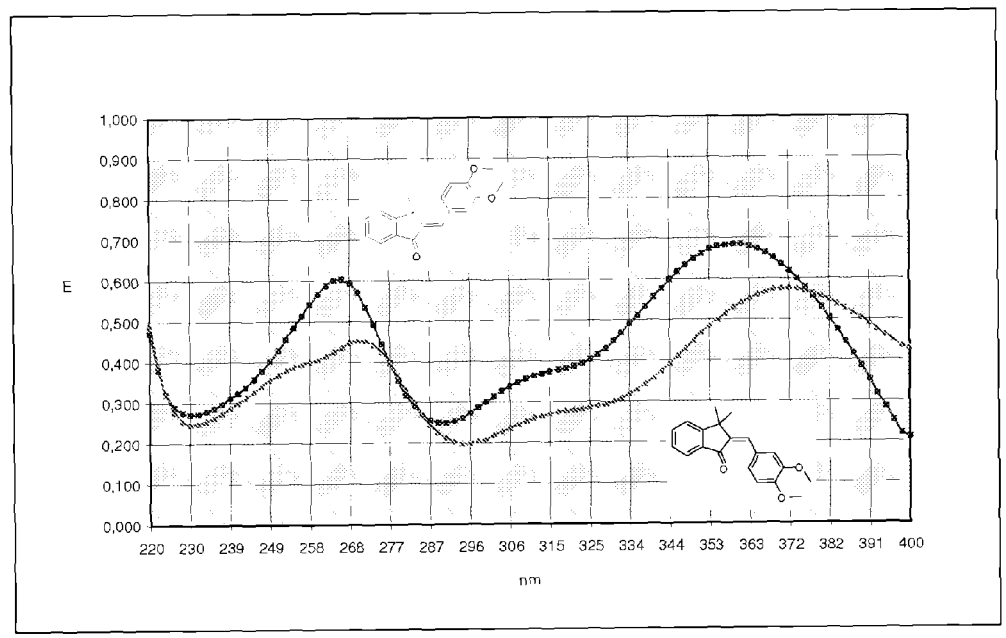
FIG. 2 shows the UV absorption spectra of each of the compounds (Ib) separately in the form of the (E) or (Z) isomer (1% solution in ethanol, 1 cm path length).

B16V mouse melanoma cells are inoculated into a 96-well microtitre plate in a concentration of $5 \times 10^3$ cells/well. After cultivation for 24 h at 37° C. and 5% $CO_2$ in RPMI medium enriched with 10% of foetal calf serum, different concentrations of the test substances, 0.3 mM tyrosine and 10 nM α-MSH (α-melanocyte stimulating hormone) are added and incubation is continued for 96 h. Standards are incubated with kojic acid in concentrations of 0.01 mM, 0.1 mM and 1 mM, together with tyrosine and α-MSH. Only tyrosine and α-MSH are added to the controls. After incubation, sodium laurylsulfate and sodium hydroxide solution (final concentrations: 1 mM and 1 M respectively) are added to the culture medium and the absorption (A) is measured at 400 nm after 3 h.

The inhibition of pigmentation in the presence of the test compounds or kojic acid were calculated using the following equation:

$$\text{inhibition of pigmentation (\%)} = 100 - [(A_{test\ compound}/A_{control}) \times 100]$$

The inhibition of pigmentation (%) in a number of dilutions of test compounds is used to calculate the $IC_{50}$ for each test compound. This is the concentration of a test compound at which pigmentation is 50% inhibited.

TABLE 2

| Test substance | $IC_{50}$ (µM) |
|---|---|
| Kojic acid | 452.3 |
| Compound (Ia) | 2.67 |

These data show that the depigmenting effect of the compound (Ia) according to the invention on B16V melanoma cells is about 170 times greater than that of kojic acid.

Formulation 1: "water-in-oil" emulsion with UVA/B broadband protection

Formulation 2: "oil-in-water" emulsion with UVA/B broadband protection

Formulation 3: "oil-in-water" emulsion with UVA/B broadband protection
Formulation 4: oil-free sun spray with UVA/B broadband protection
Formulation 5: balm with UVA/UVB protection
Formulation 6: aerosol foam with UVB/UVA protection
Formulation 7: non-aerosol foam
Formulation 8: shampoo with UVB protection of cells
Formulation 9: hair conditioner with UVB/UVA protection
Formulation 10: O/W day cream with UVB protection of cells
Formulation 11: W/O night cream with UVB protection of cells

TABLE 3

Compositions of formulations according to the invention (Examples 1-11)

| NAME OF RAW MATERIAL (MANUFACTURER) | INCI | 1 | 2 | 3 | 4 | 5 | 6 | 7 | 8 | 9 | 10 | 11 |
|---|---|---|---|---|---|---|---|---|---|---|---|---|
| AhR antagonists | | | | | | | | | | | | |
| Benzylidenindanone (Ia) | | | 5.0 | 0.05 | 0.2 | 1.0 | 0.5 | 0.1 | | 0.2 | 1.0 | 0.2 |
| Benzylidenindanone (Ib) | | 0.1 | | 0.05 | | | | | 0.5 | | 0.5 | 0.2 |
| Other ingredients | | | | | | | | | | | | |
| Abil 100 ® (Goldschmidt) | Dimethicone | | 1.0 | 0.3 | | | | | | | | |
| Abil 350 (Degussa-Goldschmidt) | Dimethicone | | | | | | | | | | 0.5 | |
| Alpha-bisabolol, natural (Symrise) | Bisabolol | | | | | | | | | | 0.3 | 0.2 |
| Aloe Vera Gel Concentrate 10/1 (Symrise) | Water (Aqua), Aloe Barbadensis Leaf Juice | | | | | | | | | | | |
| Alugel 34 TH (Baerlocher) | Aluminium Stearate | | | | | | | | | | | 1.0 |
| Arbutin (Sabinsa) | β-Arbutin | | | | | | | | | | 1.0 | |
| Arlypon F | Laureth-2 | | | | | | | | | 2.0 | | |
| Baysilone oil M10 (GE Bayer) | Dimethicone | | | | | | | 1.0 | | | | |
| Baysilone oil PK 20 (GE Bayer) | Phenyl Trimethicone | | | | | 5.0 | | | | | | |
| Bentone Gel MIO ® (Rheox) | Mineral oil and Quaternium-18-hectorite and Propylene carbonate, Glyceryl stearate and Cetyl alcohol | | | 3.0 | | | | | | | | |
| Alpha-bisabolol (Symrise) | Bisabolol | 0.1 | | 0.1 | | 0.2 | 0.1 | 0.1 | 0.1 | | | |
| 1,3-Butylene glycol | 1,3-Butylene glycol | | | 3.0 | | | | | | | | |
| Carbopol 2050 ® (B.F. Goodrich) | Carbomer | | | 0.2 | | | 0.1 | | | | | |
| Carbopol ETD 2001 (Noveon) | Carbomer | | | | | 0.5 | | | | | | |
| Ceramide 2 (Sederma) | Ceramide 2 | | | | | | | | | | 0.1 | |
| Ceramide SL (Sino Lion) | Hydroxyethyl Palmityl Oxyhydroxypropyl Palmitamide | | | | | | | | | | | 0.1 |
| Cetiol SN ® (Cognis) | Cetyl and Stearyl isononanoate | 5.0 | 4.0 | 5.0 | | | | | | | | |
| Cetiol OE (Cognis) | Dicaprylyl Ether | | | | | | | 3.0 | | | | |
| Citric Acid | Citric Acid | | | | | | | | | 0.1 | | |
| Copherol 1250 ® (Cognis) | Tocopherol acetate | 1.0 | | 0.5 | | 0.5 | 0.5 | 0.5 | | | | |
| Corapan TQ ® (Symrise) | Diethylhexyl 1,6-Naphthalate | | | | 3.0 | | | | | | | |
| Crinipan ®AD (Symrise) | Climbazole | | | | | | | | | 0.5 | | |
| Crotein Q (Croda) | Hydroxypropyl trimonium Hydrolysed | | | | | | | | | 1.0 | | |

TABLE 3-continued

Compositions of formulations according to the invention (Examples 1-11)

| NAME OF RAW MATERIAL (MANUFACTURER) | INCI | Wt. % | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Cutina CBS ® (Cognis) | Glyceryl stearate and Cetyl alcohol and Stearyl alcohol and Cetyl palmitate and Coconut glyceride | | 2.0 | | | | | | | | | |
| Dehymuls PGPH ® (Cognis) | Polyglycerol-2 Dipolyhydroxystearate | 3.0 | | | | | | | | | | |
| Dehyquart SP | Quaternium-52 | | | | | | | | | | 0.5 | |
| Dehyton K | Cocamidopropyl Betaine | | | | | | | | 12.0 | | | |
| Dow Corning ® 193 (Dow Corning) | Dimethicone-Polyol | | | | | 1.0 | | | | | | |
| Dow Corning 200 Fluid (Dow Corning) | Dimethicone | | | | | | | | | | | |
| D-Panthenol (BASF) | Panthenol | | | | | 0.5 | | | 0.5 | 0.4 | | |
| Dracorin 100 s.e. ® (Symrise) | Glyceryl stearate (and) PEG-100 Stearate | | | 3.0 | | | | | | | | |
| Dracorin CE (Symrise) | Glyceryl Stearate Citrate | | | | | | | | | | 5.0 | |
| Dragocid Liquid (Symrise) | Phenoxyethanol (and) Methylparaben (and) Ethylparaben (and) Butylparaben (and) Propylparaben (and) Isobutylparaben | 0.3 | 0.3 | 0.3 | | 0.3 | 0.3 | 0.3 | | 0.5 | | 0.8 |
| Drago-Beta-Glucan (Symrise) | Water (Aqua), Butylene Glycol, Glycerol, *Avena Sativa* (Oat) Kernel Extract | | | | | | | | | 0.3 | | |
| Dragoderm (Symrise) | Glycerol, *Triticum Vulgare* (Wheat) Gluten, Water (Aqua) | | | | | | | | | 2.0 | | |
| Dragophos S (Symrise) | Sodium Dihydroxycetyl Phosphate | | | | | | | | | | | |
| Dragorin GMS (Symrise) | Glyceryl Stearate | | | 2.0 | | | 2.0 | | | | | |
| Dragosan W/O Liquid (Symrise) | Polyglyceryl-3-Polyricinoleate, Sorbitan Isostearate | | | | | | | | | | | 1.0 |
| Dragosan W/O P (Symrise) | Sorbitan Isostearate, Hydrogenated Castor Oil, Ceresin, Beeswax (*Cera Alba*) | | | | | | | | | | | 6.0 |
| Dragoxat EH (Symrise) | Ethylhexyl Ethylhexanoate | | | | | | | | | | 3.0 | |
| Edeta BD ® (BASF) | Disodium EDTA | 0.1 | 0.1 | 0.1 | | 0.1 | 0.1 | 0.1 | | | | |
| Emulgin B2 ® (Cognis) | Ceteareth-20 | | 1.0 | | | | | | | 0.7 | | |
| Emulsiphos (Symrise) | Cetyl phosphate, Hydrogenated Palm glycerides | | | | 1.5 | | 1.5 | | | | | |

TABLE 3-continued

Compositions of formulations according to the invention (Examples 1-11)

| NAME OF RAW MATERIAL (MANUFACTURER) | INCI | 1 | 2 | 3 | 4 | 5 | 6 | 7 | 8 | 9 | 10 | 11 |
|---|---|---|---|---|---|---|---|---|---|---|---|---|
| Ethanol (96%) | Ethyl alcohol | | | | 13.0 | 5.0 | | | | | | |
| Euxyl K 100 ® (Schülke & Mayr) | Methylchloroiso-thiazolinone, Methylisothiazolinone | | | | 0.1 | | | | | | | |
| Extrapon Aloe Vera (Symrise) | Aqua, Aloe Barbadensis, Propylene Glycol, Alcohol | | | | 1.0 | | | | | | | |
| Extrapon Kamille (Symrise) | Glycerol, Water (Aqua), Chamomilla Recutita (Matricaria) Flower Extract | | | | 1.0 | | | | | | | |
| Extrapon Hamamelis (Symrise) | Propylene Glycol, Hamamelis Virginiana (Witch Hazel) Water, Water (Aqua), Alcohol, Hamamelis Virginiana (Witch Hazel) Bark/Leaf/Twig Extract | | | | 1.0 | | | | | | | |
| Glycerol 85% | Glycerol | | | | | | | | | | 3.0 | 2.0 |
| Glycerol 99% | Glycerol | 4.0 | 3.0 | | 4.5 | | 3.0 | 4.0 | | | | |
| Hydrolite-5 (Symrise) | 1,2-Pentanediol | | | | | 4.0 | | 5.0 | | | | |
| Isodragol (Symrise) | Triisononanoin | | | | | | | | | | | |
| Isopropyl myristate (Symrise) | Isopropyl Myristate | | | | | | | | | | | |
| Isopropyl palmitate (Symrise) | Isopropyl Palmitate | | | | | | | | | | 4.0 | |
| Karion F (Merck) | Sorbitol | | | | | | | | | | | 2.0 |
| Keltrol RD (CP-Kelco) | Xanthan Gum | | | | | | | | | | 0.2 | |
| Keltrol T ® (Calgon) | Xanthan Gum | | | 0.2 | 0.2 | 0.3 | | | | | | |
| Kojic Acid (Cosmetochem) | Kojic Acid | | | | | | | | | | 1.0 | |
| Lanette E ® (Cognis) | Sodium cetearylsulfate | | | | 0.7 | | | | | | | |
| Lanette O ® (Cognis) | Cetyl and Stearyl alcohol | | 1.1 | | | | | | | 2.5 | | |
| Lanette 16 ® (Cognis) | Cetyl alcohol | | | | 1.2 | | 0.5 | | | | 1.0 | |
| Lanette 18 (Care Chemicals) | Stearyl Alcohol | | | | | | | | | | 4.5 | |
| Lara Care A-200 (Rahn) | Galactoarabinan | | | | | | | 0.2 | | | | |
| Mg Ascorbyl-phosphate | Magnesium Ascorbyl-phosphate | | | | | | | | | | 3.0 | |
| Magnesium Chloride (Merck) | Magnesium Chloride | | | | | | | | | | | 0.7 |
| Monomuls 90-O 18 ® (Cognis) | Glyceryl oleate | 1.0 | | | | | | | | | | |
| Myritol 318 ® (Cognis) | Caprylic/Capric triglycerides | 6.0 | 5.0 | | | | | | | | | |
| NaOH 10% aq. solution | Sodium hydroxide | | | 2.8 | | 2.2 | 2.9 | 0.6 | | | | |
| Sodium Ascorbyl-Phosphate (EMD Chemicals) | Sodium Ascorbyl-phosphate | | | | | | | | | | 2.0 | |

TABLE 3-continued

Compositions of formulations according to the invention (Examples 1-11)

| NAME OF RAW MATERIAL (MANUFACTURER) | INCI | Wt. % | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Natrosol 250 HHR (Aqualon) | Hydroxymethyl cellulose | | 0.3 | | | | | | | | | |
| Neo-Dragocid powder(Symrise) | Methylparaben, Sorbic Acid, Dehydroacetic Acid, Propylparaben | | | | | | | | | | | |
| Neo Heliopan ® AP (Symrise), 15% as sodium salt | Disodium phenyl-dibenzimidazole-tetrasulfonate | 10.0 | | 22.0 | | | | | | | | |
| Neo Heliopan ® AP (Symrise), 10% aq. solution neutralized with NaOH | Disodium phenyl-dibenzimidazole-tetrasulfonate | | | | 22.0 | | | | | | | |
| Neo Heliopan ® AV (Symrise) | Ethylhexyl methoxycinnamate | 4.0 | | | | 5.0 | 6.0 | 2.0 | | | | |
| Neo Heliopan ® BB (Symrise) | Benzophenone-3 | | 1.0 | | | | | | | | | |
| Neo Heliopan ® 303 (Symrise) | Octocrylene | | 7.0 | | | | | | | | | |
| Neo Heliopan ® 357 (Symrise) | Butylmethoxy-dibenzoylmethane | | | | 2.0 | 1.5 | 1.5 | 1.5 | 0.5 | 0.5 | | |
| Neo Heliopan ® E 1000 (Symrise) | Isoamyl p-methoxy-cinnamate | 4.0 | | | | 5.0 | | 6.0 | | 2.0 | | |
| Neo Heliopan ® HMS (Symrise) | Homosalate | | | | 5.0 | | | | | | | |
| Neo Heliopan ® Hydro (15% aq. solution neutralized with NaOH) (Symrise) | Phenylbenzimidazolesulfonic acid | | | | | 33.3 | 10.0 | 13.3 | | 3.3 | | |
| Neo Heliopan ® MA (Symrise) | Menthyl anthranilate | | 3.0 | | | | | | | | | |
| Neo Heliopan ® MBC (Symrise) | 4-Methyl-benzylidenecamphor | 2.0 | | | | 2.0 | 4.0 | 3.0 | | | | |
| Neo Heliopan ® OS (Symrise) | Ethylhexyl salicylate | 3.0 | | | | | | | | | | |
| Neutral oil (Symrise) | Caprylic/capric triglycerides | | | | 5.0 | | 2.0 | | | | 6.0 | |
| Octyltriazone | Ethylhexyltriazone | 1.0 | | | | | | | | | | |
| Oxynex 2004 (Merck) | BHT | | | | | | | | | | | 0.1 |
| Paraffin Oil 5 Grade E (Parafluid) | Paraffinum Liquidum | | | | | | | | | | | |
| Perfume Oil (Symrise Fragrance) | Perfume (Fragrance) | 0.3 | 0.3 | 0.3 | | 0.3 | 0.4 | 0.2 | 0.5 | 0.4 | 0.3 | 0.,4 |
| PCL Liquid (Symrise) | Cetearyl Ethylhexanoate, Isopropyl Myristate | | | | | | | | | | | 12.0 |
| PCL Liquid 100 (Symrise) | Cetearyl Ethylhexanoate | | | | | | | | | | 3.0 | |
| Pemulen TR 2 (Novion) | Acrylates/C10-30 Alkyl Acrylate Crosspolymer | | | | | | | | 0.2 | | | |
| Permulgin 2550 ® (Koster Keunen) | Bees Wax | 1.0 | | | | | | | | | | |
| Phenoxyethanol (Symrise) | Phenoxyethanol | 0.7 | | 0.7 | | 0.7 | 0.7 | 0.7 | | | | |
| Polymer JR 400 | Polyquaternium-10 | | | | | | | | | 0.4 | | |
| 1,2-Propylene glycol | Propylene Glycol | | | | | | | | | | | |

TABLE 3-continued

Compositions of formulations according to the invention (Examples 1-11)

| NAME OF RAW MATERIAL (MANUFACTURER) | INCI | Wt. % | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Retinyl Palmitate in Oil (DSM Nutritional Products) | Retinyl Palmitate | | | | | | | | | | | 0.2 |
| Softigen 767 | PEG-6 Caprylic/Capric Glycerides | | | | | | | | 2.5 | | | |
| Solubilizer (Symrise) | PEG 40 Hydrogenated Castor Oil, Trideceth-9, Propylene glycol, Water | | | | | | | | 3.0 | | | |
| Sun Flower Oil (Wagner) | *Helianthus Annuus* (Sunflower) Seed Oil | | | | | | | | | | | 5.0 |
| Sweet Almond Oil (Wagner) | *Prunus dulcis* | | | | | | | | | | | 5.0 |
| SymCalmin | Butylene Glycol, Pentylene Glycol, Hydroxyphenyl Propamidobenzoic Acid | | | 0.5 | | | | | | | | |
| Symdiol 68 (Symrise) | 1,2-Hexanediol, Caprylyl glycol | | | 0.5 | | | | | | | 0.5 | |
| SymMatrix (Symrise) | Maltodextrin, *Rubus Fruticosus* (Blackberry) Leaf Extract | | | | | | | | | | | 1.0 |
| SymWhite 377 | 4-(1-Phenylethyl)-1,3-benzenediol | | | | | | | | | | 0.5 | |
| Tegosoft TN ® (Goldschmidt) | C12-C15 Alkyl benzoates | 6.0 | | | | 4.0 | 2.0 | | | | | |
| Texapon N 70 (Cognis) | Sodium Laureth Sulfate | | | | | | | 0.1 | 0.5 | | | |
| Texapon NSO BZ (Cognis) | Sodium Laureth Sulfate | | | | | | | | 27.0 | | | |
| Titanium dioxide microfine | Titanium dioxide | | 5.0 | | | | | | | | | |
| Tocopherol Acetate (DSM Nutritional Products) | Tocopheryl Acetate | | | | | | | | | | | 3.0 |
| Unimer U-151 (Induchem) | PVP/Hexadecene Copolymer | | | | | | 0.5 | | | | | |
| Veegum ultra ® (Vanderbilt) | Magnesium Aluminium sulphate | | 1.0 | | | | | | | | | |
| Witch Hazel Distillate (Symrise) | *Hamamelis Virginiana* (Witch Hazel) | | | | | | | | 1.0 | | | |
| Zinc oxide neutral (Symrise) | Zinc oxide | 7.0 | | | | | | | | | | |
| Water, dist. | Aqua (Water) | ad 100 | ad 100 | ad 100 | ad 100 | ad 100 | ad 100 | ad 100 | ad 100 | Ad 100 | ad 100 | ad 100 |

Specific Embodiments

Specific embodiment one comprises a compound of formula (I):

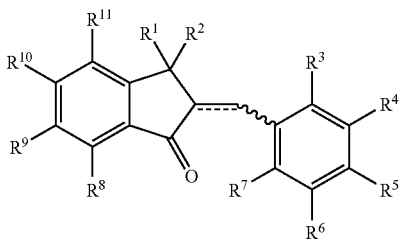

in which

R$^1$ and R$^2$ independently of one another are hydrogen or C$_1$-C$_{12}$-alkyl, R$^3$ to R$^{11}$ independently of one another are hydrogen, C$_1$-C$_{12}$-alkyl, hydroxyl or C$_1$-C$_{12}$-alkoxy, and the broken line represents either a double bond or two hydrogens, as a drug.

Specific embodiment two comprises a compound of formula (Ia), (Ib), (Ic) and/or (Id):

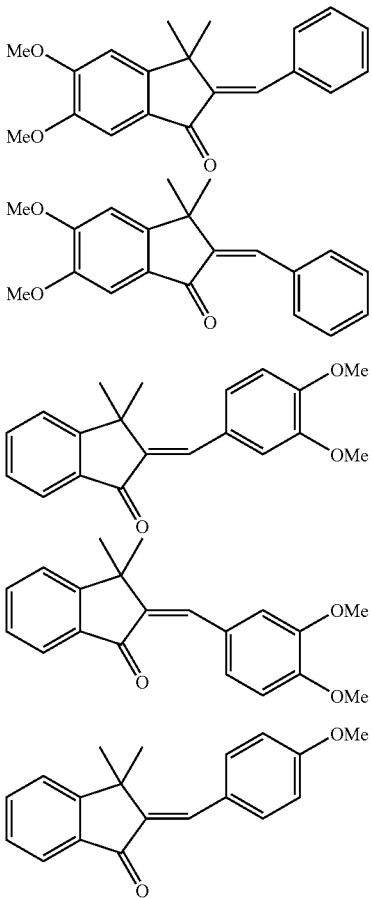

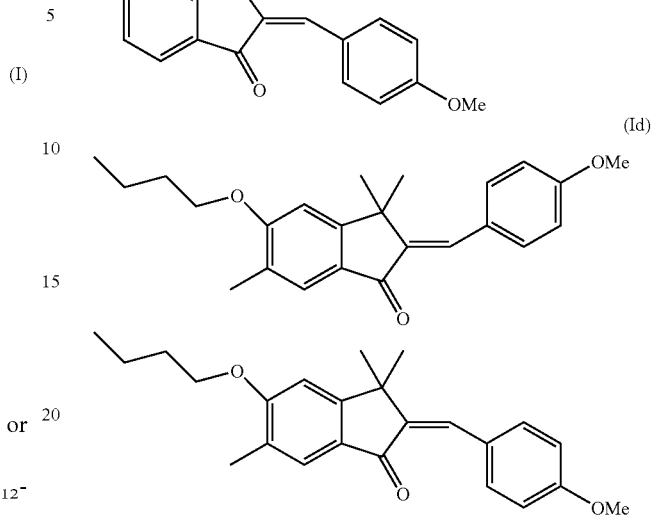

as a drug.

Specific embodiment three comprises a compound of formula (I) in which R$^1$ and R$^2$ independently of one another are C$_1$-C$_{12}$-alkyl.

Specific embodiment four comprises a compound according to specific embodiment three in which R$^1$ and R$^2$ are methyl.

Specific embodiment five comprises a compound according to specific embodiment three of formula (Ia), (Ib), (Ic) and (Id):

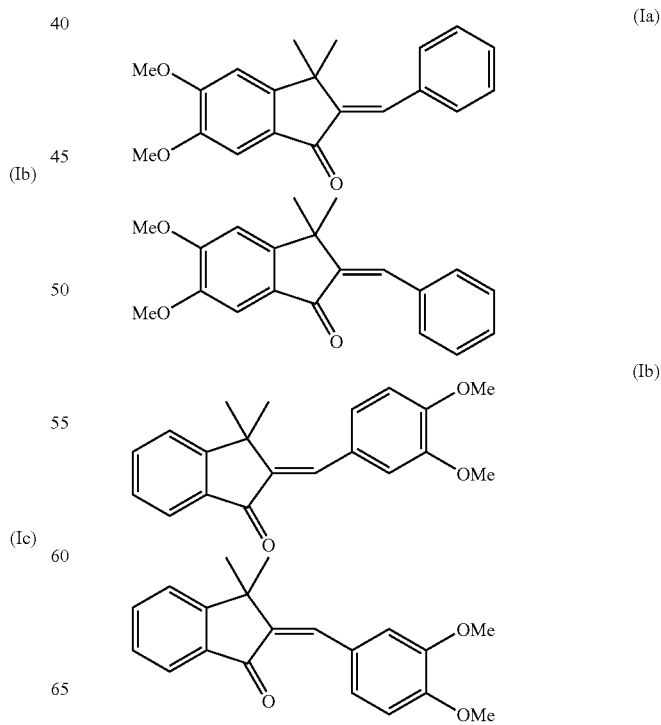

-continued

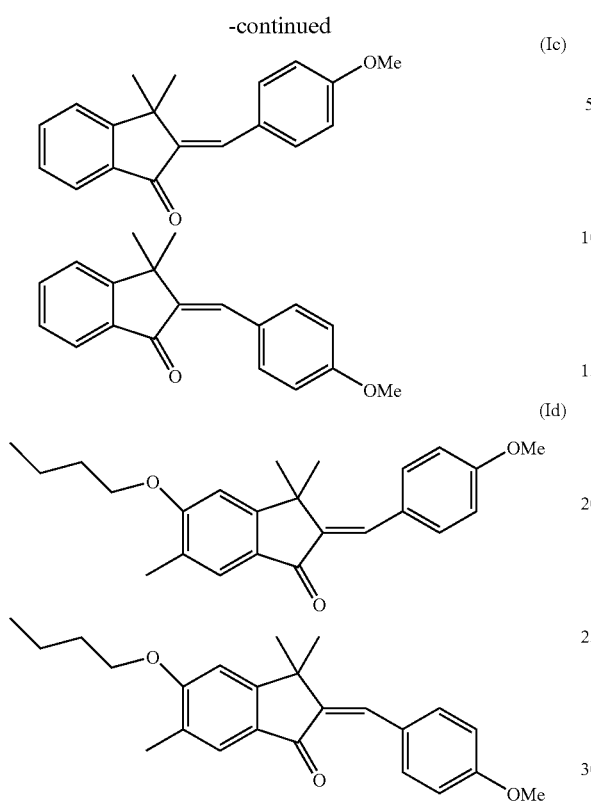

Specific embodiment six comprises a formulation containing a compound of formula (I), preferably of formula (Ia), (Ib), (Ic) or (Id), in a sufficient amount (a) for reducing or preventing a translocation of the AhR into a cell nucleus, (b) for reducing or preventing a UVB-induced gene expression, (c) for reducing or preventing a gene expression induced or inducible by polycyclic aromatic hydrocarbons, preferably TCDD, and/or (d) for reducing or preventing UVB-induced or UVB-inducible skin damage, especially skin cancer, skin ageing, skin inflammations and sunburn.

Specific embodiment seven comprises a formulation according to specific embodiment six which also comprises one or more UV filters, especially one or more UVB filters and/or one or more UVA filters.

Specific embodiment eight comprises use of a compound of formula (I), preferably of formula (Ia), (Ib), (Ic) or (Id), or a formulation according to specific embodiment six or seven, as a skin protection agent, photoprotective agent and/or AhR antagonist.

Specific embodiment nine comprises use of a compound of formula (I), preferably of formula (Ia), (Ib), (Ic) or (Id), or a formulation according to specific embodiment six or seven for the preparation of a drug.

Specific embodiment ten comprises use of a compound of formula (I), preferably of formula (Ia), (Ib), (Ic) or (Id), for the preparation of a formulation (a) for reducing or preventing a translocation of the AhR into a cell nucleus, (b) for reducing or preventing a UVB-induced gene expression, (c) for reducing or preventing a gene expression induced or inducible by polycyclic aromatic hydrocarbons, preferably TCDD, and/or (d) for reducing or preventing UVB-induced or UVB-inducible skin damage, especially skin cancer, skin ageing, skin inflammations and sunburn.

Specific embodiment eleven comprises a cosmetic method of protecting the skin, characterized in that a compound of formula (I), preferably of formula (Ia), (Ib), (Ic) or (d), or a formulation according to specific embodiment six or seven is applied to the skin to be protected.

Specific embodiment twelve comprises a process for the preparation of a compound of formula (I), preferably of formula (Ia), (Ib), (Ic) or (Id), comprising the following steps:

Reaction of an Indanone and an Aromatic Aldehyde According to the Scheme

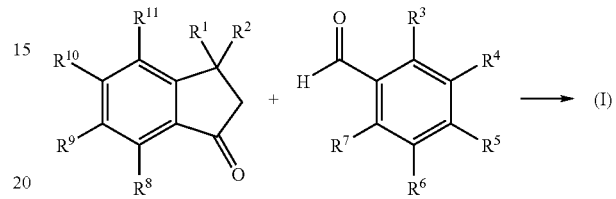

in which the radicals $R^1$ to $R^{10}$ are as defined in specific embodiment one.

The invention claimed is:
1. A compound of formula (Ia), (Ib), or (Id):

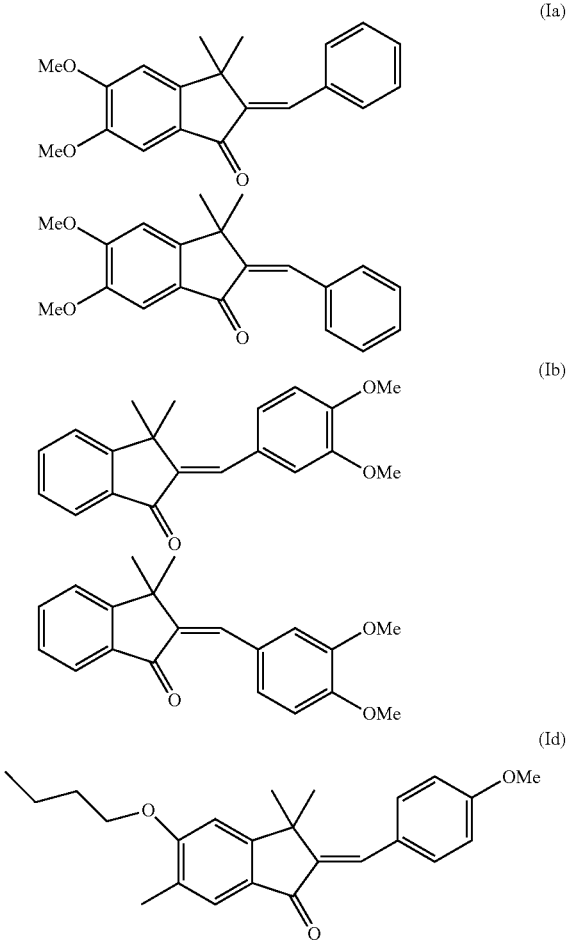

-continued

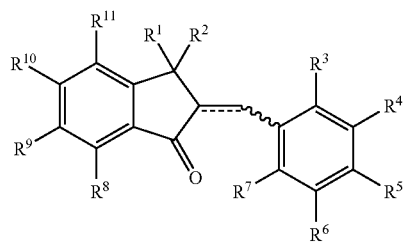

2. A process for the preparation of a compound according to claim 1 comprising reacting an indanone and an aromatic aldehyde according to the scheme

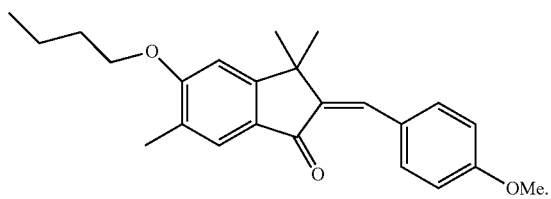

in which,
for formula (Ia): $R^1$ and $R^2$ =CH$_3$; $R^3$-$R^8$ and $R^{11}$=H; $R^9$ and $R^{10}$=methoxy;
for formula (Ib): $R^1$ and $R^2$ =CH$_3$; $R^3$, $R^6$-$R^{11}$=H; $R^4$ and $R^5$=methoxy; and
for formula (Id): $R^1$, $R^2$ and $R^9$ =CH$_3$; $R^3$-$R^4$, $R^6$-$R^8$ and $R^{11}$=H; $R^{10}$=butoxy; and
$R^5$=methoxy.

3. A pharmaceutical formulation comprising a compound of formula (I):

(I)

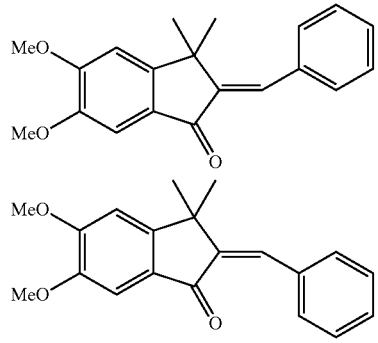

in which
$R^1$ and $R^2$ independently of one another are $C_1$-$C_{12}$-alkyl;
$R^3$ to $R^{11}$ independently of one another are hydrogen, $C_1$-$C_{12}$-alkyl, hydroxyl or $C_1$-$C_{12}$-alkoxy; and
the broken line represents either a double bond or two hydrogens.

4. The pharmaceutical formulation according to claim 3 in which $R^1$ and $R^2$ are methyl.

5. The pharmaceutical formulation according to claim 3, wherein the compound of formula (I) is compound of formula (Ia), (Ib), (Ic), or (Id):

(Ia)

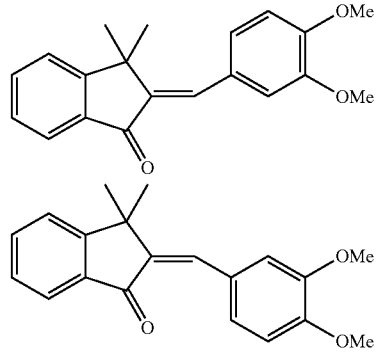

(Ib)

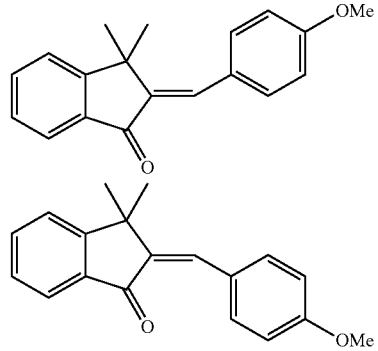

(Ic)

(Id)

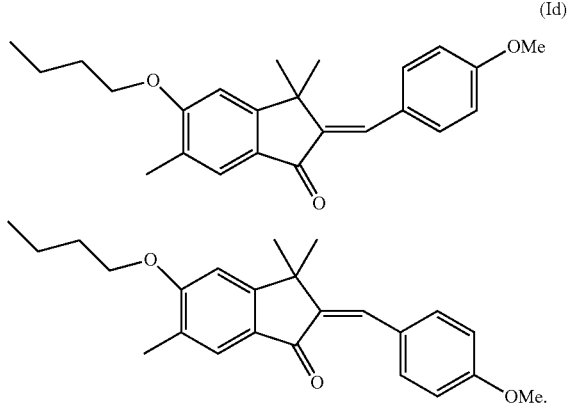

6. The pharmaceutical formulation according to claim 3, wherein the compound of formula (I) is in a sufficient amount (a) for reducing or preventing a translocation of an AhR into a cell nucleus, (b) for reducing or preventing a UVB-induced gene expression, (c) for reducing or preventing a gene expression induced or inducible by polycyclic aromatic hydrocarbons and/or (d) for reducing or preventing UVB-induced or UVB-inducible skin damage.

7. The pharmaceutical formulation according to claim 6 for reducing or preventing gene expression induced or inducible by polycyclic aromatic hydrocarbons, wherein the polycyclic aromatic hydrocarbon is 2,3,7,8-tetrachlorodibenzo-p-dioxin (TCDD) or 6-formylindolo[3,2-b]carbazole (FICZ).

8. The pharmaceutical formulation according to claim 6 for reducing or preventing UVB-induced or UVB-inducible skin damage, wherein the skin damage is skin cancer, skin ageing, skin inflammation, or sunburn.

9. A pharmaceutical formulation for reducing or preventing a gene expression induced or inducible by 2,3,7,8-tetrachlorodibenzo-p-dioxin (TCDD) comprising a compound of formula (I):

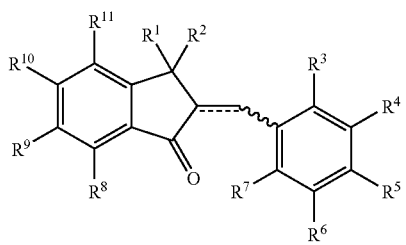

in which

R$^1$ and R$^2$ independently of one another are C$_1$-C$_{12}$-alkyl;

R$^3$ to R$^{11}$ independently of one another are hydrogen, C$_1$-C$_{12}$-alkyl, hydroxyl or C$_1$-C$_{12}$-alkoxy; and the broken line represents either a double bond or two hydrogens.

10. A skin protection agent, photoprotective agent, and/or AhR antagonist comprising a compound of formula (I):

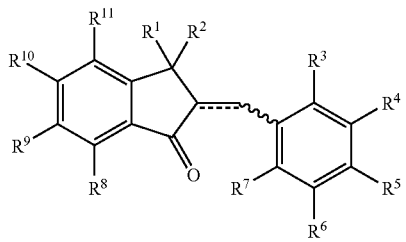

in which

R$^1$ and R$^2$ independently of one another are C$_1$-C$_{12}$-alkyl;

R$^3$ to R$^{11}$ independently of one another are hydrogen, C$_1$-C$_{12}$-alkyl, hydroxyl or C$_1$-C$_{12}$-alkoxy; and the broken line represents either a double bond or two hydrogens; and one or more UV filters.

11. The skin protection agent, photoprotective agent, and/or AhR antagonist according to claim 10 in which R$^1$ and R$^2$ are methyl.

12. The skin protection agent, photoprotective agent, and/or AhR antagonist according to claim 10, wherein the compound of formula (I) is a compound of formula (Ia), (Ib), (Ic), or (Id):

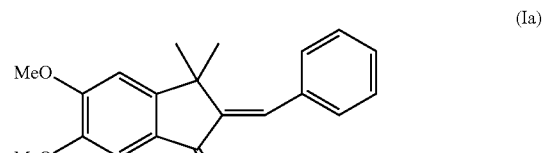
(Ia)

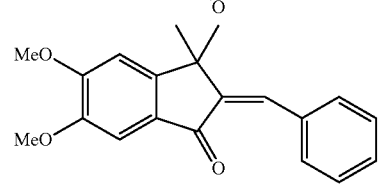
(Ib)

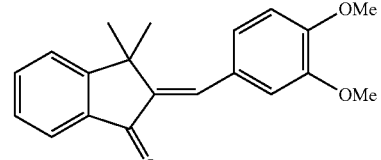

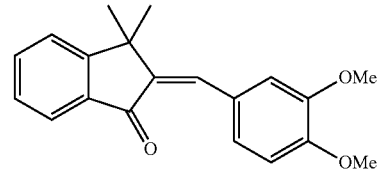
(Ic)

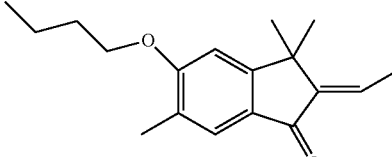
(Id)

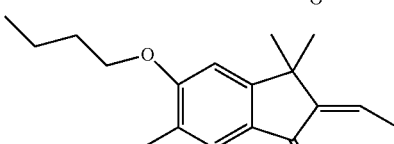

13. A method (a) for reducing or preventing a translocation of an AhR into a cell nucleus, (b) for reducing or preventing a UVB-induced gene expression, (c) for reducing or preventing a gene expression induced or inducible by polycyclic aromatic hydrocarbons and/or (d) for reducing or preventing UVB-induced or UVB-inducible skin damage comprising applying to the skin a compound of formula (I):

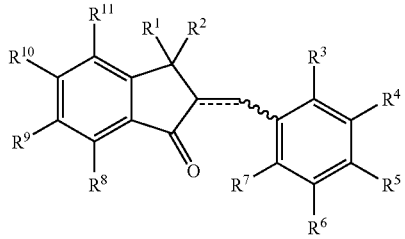

in which

R¹ and R² independently of one another are $C_1$-$C_{12}$-alkyl;
R³ to R¹¹ independently of one another are hydrogen, $C_1$-$C_{12}$-alkyl, hydroxyl or $C_1$-$C_{12}$-alkoxy; and
the broken line represents either a double bond or two hydrogens.

14. The method according to claim 13 in which R¹ and R² are methyl.

15. The method according to claim 13, wherein the compound of formula (I) is a compound of formula (Ia), (Ib), (Ic), or (Id):

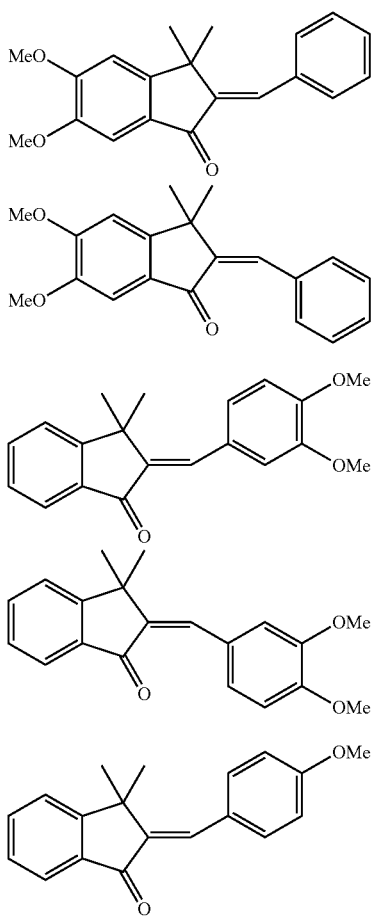

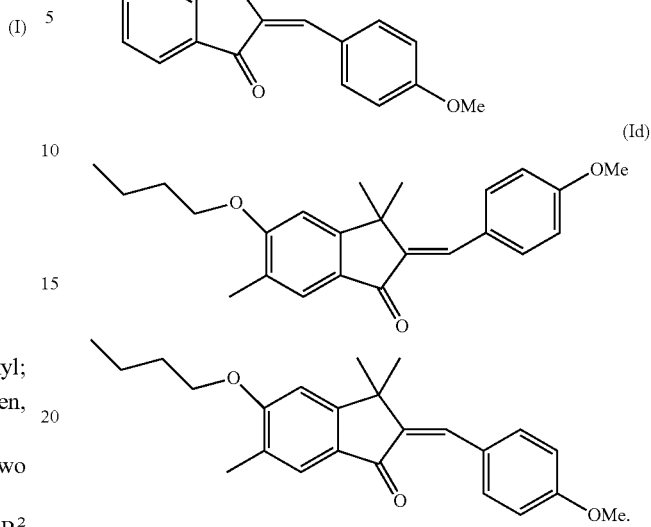

16. The method of claim 13 for reducing or preventing gene expression induced or inducible by polycyclic aromatic hydrocarbons, wherein the polycyclic aromatic hydrocarbon is 2,3,7,8-tetrachlorodibenzo-p-dioxin (TCDD) or 6-formylindolo[3,2-b]-carbazole (FICZ).

17. The method of claim 13 for reducing or preventing UVB-induced or UVB-inducible skin damage, wherein the skin damage is skin cancer, skin ageing, skin inflammation, or sunburn.

18. A method for reducing or preventing a gene expression induced or inducible by 2,3,7,8-tetrachlorodibenzo-p-dioxin (TCDD) comprising applying to the skin a compound of formula (I):

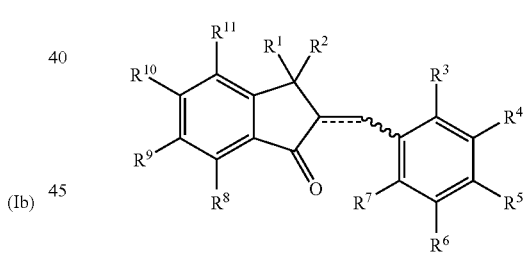

in which

R¹ and R² independently of one another are $C_1$-$C_{12}$-alkyl;
R³ to R¹¹ independently of one another are hydrogen, $C_1$-$C_{12}$-alkyl, hydroxyl or $C_1$-$C_{12}$-alkoxy; and
the broken line represents either a double bond or two hydrogens.

19. A cosmetic method of protecting the skin comprising applying to the skin a compound of formula (I):

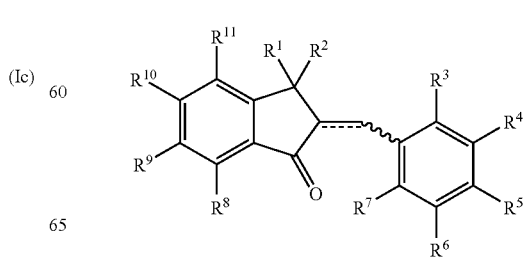

in which $R^1$ and $R^2$ independently of one another are $C_1$-$C_{12}$-alkyl;

$R^3$ to $R^{11}$ independently of one another are hydrogen, $C_1$-$C_{12}$-alkyl, hydroxyl or $C_1$-$C_{12}$-alkoxy; and the broken line represents either a double bond or two hydrogens.

20. The cosmetic method according to claim 19, wherein $R^1$ and $R^2$ are methyl.

21. The cosmetic method according to claim 19, wherein the compound of formula (I) is a compound of formula (Ia), (Ib), (Ic), or (Id):

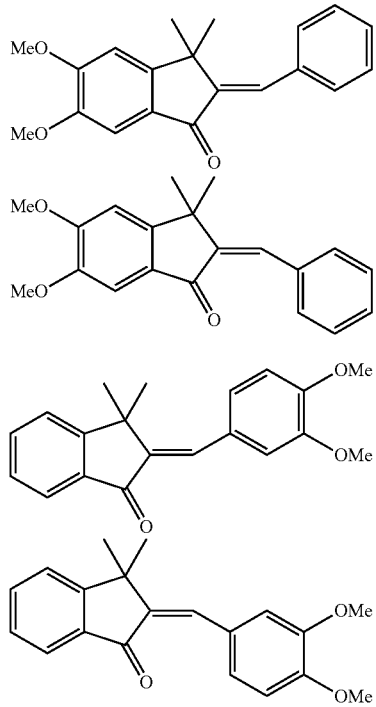

(Ia)

(Ib)

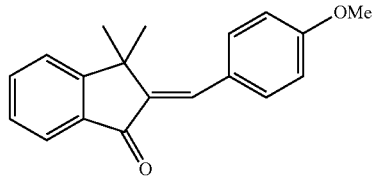

(Ic)

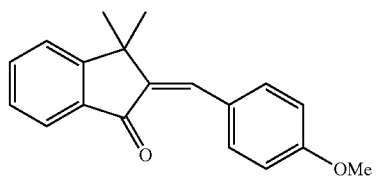

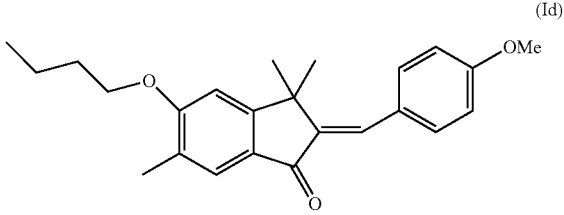

(Id)

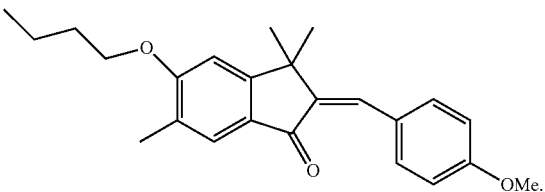

* * * * *